United States Patent
Parker et al.

(10) Patent No.: US 6,443,164 B1
(45) Date of Patent: *Sep. 3, 2002

(54) APPARATUS FOR AUTOMATIC APPLICATION OF COMPOSITIONS TO THE SKIN

(75) Inventors: Anthony Joseph Parker, Greenfield; Neil Andrew Flack; Martin Howard Miller, both of Carmel, all of IN (US)

(73) Assignee: Spectrum Products, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/802,078

(22) Filed: Mar. 8, 2001

Related U.S. Application Data

(63) Continuation-in-part of application No. 09/668,247, filed on Sep. 22, 2000.

(51) Int. Cl.$^7$ .............................................. A45D 44/00
(52) U.S. Cl. ........................... 132/333; 132/320; 4/525; 4/597; 119/671; 601/160
(58) Field of Search ................................. 132/320, 333; 4/524, 525, 528, 531, 596, 597, 602, 603, 611, 612, 615, 616; 119/604, 665–671, 678; 604/19; 601/154–156, 160; 600/21

(56) References Cited

U.S. PATENT DOCUMENTS

| | | |
|---|---|---|
| 62,916 A | 3/1867 | Allen et al. |
| 366,164 A | 7/1887 | Gillam |
| 870,766 A | 11/1907 | Eaton |
| 1,262,638 A | 4/1918 | Class |
| 1,982,509 A | 11/1934 | Frank ............................ 128/1 |
| 2,949,403 A | 8/1960 | Andreadis et al. ............. 167/90 |
| 3,421,692 A | 1/1969 | Babington et al. ............. 239/8 |
| 3,647,143 A | 3/1972 | Gauthier et al. ............. 239/342 |
| 3,649,299 A | 3/1972 | Sholl ............................ 99/107 |
| 3,762,402 A | 10/1973 | Abramovitz .................. 128/33 |
| 3,815,595 A | 6/1974 | Bar ............................ 128/184 |
| 3,868,950 A | 3/1975 | Kato ............................ 128/66 |
| 4,322,037 A | 3/1982 | Heeb et al. .................. 239/337 |
| 4,368,776 A | 1/1983 | Negita et al. ............... 165/133 |
| 4,376,437 A | 3/1983 | Sundheim et al. ......... 128/82.1 |
| 4,409,694 A | 10/1983 | Barrett, Sr. et al. ............. 4/545 |
| 4,424,598 A | 1/1984 | Cima ............................ 4/524 |
| 4,483,636 A | 11/1984 | Meyer ........................ 401/266 |
| 4,573,639 A | 3/1986 | Logue ........................ 239/428 |
| 4,644,592 A | * 2/1987 | Small ............................ 4/583 |
| 4,689,258 A | * 8/1987 | Slosgerg et al. ............. 428/141 |
| 4,749,130 A | 6/1988 | Utzinger ..................... 239/543 |
| 4,801,459 A | 1/1989 | Liburdy ....................... 424/450 |
| 4,832,943 A | 5/1989 | Grollier et al. ............... 424/59 |
| 4,858,256 A | 8/1989 | Shankman ..................... 4/597 |
| 4,869,612 A | 9/1989 | Mooney et al. ............. 401/130 |
| 4,941,618 A | 7/1990 | Hildebrand et al. ........ 239/432 |
| 5,065,942 A | 11/1991 | Shannon ..................... 239/282 |
| 5,076,266 A | 12/1991 | Babaev ........................ 128/200 |

(List continued on next page.)

*Primary Examiner*—Pedro Philogene
(74) *Attorney, Agent, or Firm*—Woodward, Emhardt, Naughton, Moriarty & McNett

(57) ABSTRACT

An apparatus is described for the coating of a human body with a tanning composition, such as a sunless tanning composition, wherein an arm with a plurality of nozzles thereon traverses within a booth to spray coat a body in the booth. The spray nozzles are oriented to avoid opposing air flows and excessive air flows which cause inefficient and uneven, dripping or streaking in the deposition of tanning composition on the skin. In another aspect, the apparatus provides for a foot rinser to rinse the feet of a user while the apparatus applies a sunless tanning composition to the user to avoid overly darkening the user's feet. In yet another aspect, the apparatus provides for a sanitation system to wash-down the spray booth between successive uses.

11 Claims, 14 Drawing Sheets

U.S. PATENT DOCUMENTS

| | | | |
|---|---|---|---|
| 5,136,735 A | 8/1992 | Zimmerman | 4/597 |
| 5,178,871 A | 1/1993 | Thill | 424/405 |
| 5,193,354 A | 3/1993 | Kleinberger et al. | 62/247 |
| 5,205,306 A | 4/1993 | Peterson | 134/104 |
| 5,235,969 A | 8/1993 | Bellm | 128/200 |
| 5,261,601 A | 11/1993 | Ross et al. | 239/102.2 |
| 5,268,166 A | 12/1993 | Barnett et al. | 424/47 |
| 5,287,569 A * | 2/1994 | Johnson | 4/603 |
| 5,305,476 A | 4/1994 | Ohyama et al. | 4/605 |
| 5,372,126 A | 12/1994 | Blau | 128/200 |
| 5,398,465 A * | 3/1995 | Tagg | 4/460 |
| 5,416,931 A | 5/1995 | Wolfenden et al. | 4/524 |
| 5,445,596 A | 8/1995 | Grace | 601/154 |
| 5,460,192 A * | 10/1995 | McClain | 132/333 |
| 5,568,669 A | 10/1996 | Godown | 15/143 |
| 5,639,441 A | 6/1997 | Sievers et al. | 424/9.3 |
| 5,657,926 A | 8/1997 | Toda | 239/102.2 |
| 5,664,593 A * | 9/1997 | McClain | 132/333 |
| 5,674,481 A | 10/1997 | Wahi | 424/78.03 |
| 5,727,541 A | 3/1998 | Rowland | 128/200.14 |
| 5,845,659 A | 12/1998 | Hutchins | 132/317 |
| 5,908,158 A | 6/1999 | Cheiman | 239/102.2 |
| 5,922,333 A | 7/1999 | Laughlin | 424/401 |
| 5,929,162 A | 7/1999 | Horne et al. | 524/731 |
| 5,945,111 A | 8/1999 | Esser | 424/401 |
| 5,970,974 A | 10/1999 | VanDerLinden et al. | 128/200.16 |
| 5,976,612 A | 11/1999 | Tardoni | 427/8 |
| 6,061,650 A * | 5/2000 | Malkin et al. | 704/228 |
| 6,121,593 A * | 9/2000 | Mansbery et al. | 219/679 |
| 6,199,557 B1 * | 3/2001 | Laughlin | 132/333 |
| 6,302,122 B1 * | 10/2001 | Parker et al. | 132/333 |

* cited by examiner

US 6,443,164 B1

APPARATUS FOR AUTOMATIC APPLICATION OF COMPOSITIONS TO THE SKIN

CROSS REFERENCE TO RELATED APPLICATIONS

This application is a continuation-in-part of pending patent application Ser. No. 09/668,247 filed Sep. 22, 2000.

FIELD OF INVENTION

This invention relates to an apparatus for the application of compositions to a person's skin, and more particularly, for example, to an apparatus adapted for use in a booth for the uniform spray application of artificial tanning compositions to the human body.

BACKGROUND OF THE INVENTION

The cosmetic effect of tanned skin has long been a desired goal for many people. This desire has led to the development of a large and varied industry supplying compositions and devices to facilitate natural or UV radiation induced tanning of the skin. Another market has developed for compositions to more rapidly provide the visual effect of tanned skin without sun exposure. In addition to the development of the multitude of sun tanning, sun screening and artificial tanning and bronzing lotions, creams and oils now available, various applicator devices for the different compositions have been devised, ranging from simple squeeze bottles and pump sprays, to hand-held spray canisters similar to pump-style pesticide spray canisters, to elaborate spray rooms that generate mists of suntan lotions or artificial tanning compositions for application to a user standing in the room.

These various applicator devices include U.S. Pat. No. 1,982,509 to Frank showing a belt-driven carriage apparatus in a vertically oriented cabinet designed to carry, among several alternatives, a compressed air sprayer head and one or more reservoirs for liquid or powder compositions to be spray applied through the sprayer head to all or part of the body of a user standing in front of the apparatus. The '509 patent does not disclose the spray application of tanning compositions, and the single spray nozzle would necessarily result in an uneven application in overlap areas as the user turns for sequential sprayer passes, and/or missed areas under the arms or on the insides of the arms and legs. The belt driven carriage of the '509 patent is raised and lowered along a guide pole in the cabinet with the start and stop positions for the carriage and the activation of the sprayer apparatus being coordinated by a complicated set of electromechanical linkages and trip-switches.

U.S. Pat. Nos. 5,460,192 and 5,664,593, both to McClain, describe variations of an apparatus to coat a user's body up to the neck with suntan lotion or sunscreen. Both variations provide for a cylindrical enclosure in which the user stands with head and neck protruding through a hole in the top of the enclosure. The apparatus of the '192 patent provides for three liquid spray nozzles directed at the shoulder level, the waist level, and at the level of the legs, respectively. When activated by a user, the apparatus sprays a dose of suntan lotion or sunscreen while the user rotates while standing. Excess spray is drained through a grating at the base of the enclosure.

The apparatus of the '593 patent atomizes the lotion into a forced-air stream which then enters the enclosure through three ports at the level of the shoulder, the waist, and the legs, respectively. An evacuation fan draws air from within the enclosure through a vent close to the base of the enclosure, creating more air turbulence in the enclosure and also recirculating excess atomized lotion from the air in the enclosure back into the forced-air stream in an effort to more efficiently and more completely coat the user's body. The user's body must still rotate within the enclosure, while the user's neck protrudes through the close fitting hole in the top of the enclosure. The apparatus of the '593 patent also collects condensed over-spray from the recirculated air with the evacuation fan mechanism, as well as draining excess over-spray from the enclosure through a grating in the enclosure base.

U.S. Pat. No. 5,922,333 to Laughlin describes a method of applying a wide variety of fluids to the body, including sunless tanning compositions, by manually directing a spray nozzle at the area to be coated, or preferably, by atomizing the fluid into an air current and directing the air current against the person being coated, and collecting the residual spray through a venting system, preferably including a filtration means.

Another apparatus presently in the marketplace provides for a booth-type enclosure with a multiplicity of fixed spray nozzles at various heights in the corners of the booth. These fixed nozzles direct a spray of artificial tanning composition at the user standing in the center of the booth. Upon completion of a spray cycle, an evacuation fan evacuates residual spray from the booth through a filtered venting system.

These devices have major drawbacks including incomplete and/or streaky application of tanning composition, inefficient use of tanning composition, discomfort for the user, difficult or inadequate sanitation of the apparatus between uses, and, when specifically used with sunless tanning compositions, do not mitigate the unsightly overstaining of the feet and toes, which are significantly more susceptible to staining by such compositions compared to other areas of the skin. The prior spray booths do not provide for complete, uniform coating. Those spray apparatuses particularly adapted for use for the application of tanning compositions produce undesirable air currents within their enclosures and around the body of a user, which currents can inhibit efficient deposition of the atomized composition on the user. These devices produce swirling clouds of liquid-laden air, but the air currents generated tend to swirl around and bypass the user's body with much of the composition being vented, drained, or deposited on the enclosing walls. The spray reaching the user's body in these prior apparatuses also tends to be subject to significant droplet coalescence adding to dripping and streaking. Thus the coatings tend to be uneven with either insufficient deposition of composition on the body and/or heavily coated areas resulting in uneven dripping and running of the composition down the body.

SUMMARY OF THE INVENTION

The present invention provides an automated apparatus for providing a more nearly uniform and efficient coating of portions of a human body, as for example, to provide more uniform coloring with artificial tanning compositions. The claims should be the guide for understanding of the scope of the invention to be protected, but the following comments may be of value in understanding the advantages that some applications of the claimed invention may provide.

The preferred design of the present invention provides a spraying apparatus for coating portions of a human body that avoids simultaneous, oppositely directed, spray directions to enhance uniformity and efficiency of the coating. The preferred design also avoids excessive air currents which produce boundary layers in front of the body and eddy currents behind the body which can inhibit efficient deposition of a sprayed composition on a human body being coated.

In another aspect of the preferred design of the invention, a spray apparatus for coating a human body with artificial tanning solution is provided, which minimizes undesirable over-staining of the feet and toes of a person being coated.

In another aspect of the invention, a spray booth for coating a human body with artificial tanning solution which includes a wash-down system is provided for easy and efficient sanitation of the booth between successive users.

In one aspect of the present invention, there is provided an apparatus for applying a tanning composition to a human body comprising a booth with a location for a human body within the booth, an arm moveably mounted within the booth, three or more active spray nozzles on the arm with none of the active spray nozzles oriented to spray in a direction substantially toward any other active spray nozzle, with the active spray nozzles being operably coupled to a source of tanning composition. In one preferred embodiment, each of the spray nozzles defines a spray direction towards the location for the person being coated and the spray directions of the nozzles are substantially parallel. In another preferred embodiment, the arm has opposing ends and defines outer portions adjacent the opposing ends and a central portion between the outer portions, and the arm has at least one spray nozzle on each of the outer portions and on the central portion of the arm, such that each spray nozzle defines a spray direction towards the location for the user, with the outer portion spray nozzles each being convergingly directed towards the location for the user at an angle between about 10 and about 20 degrees from parallel to the spray direction of the nozzle(s) on the central portion.

In another aspect of the preferred design, the booth further comprises a second arm moveably mounted within the booth having three or more second active spray nozzles on the second arm, with none of the second active spray nozzles oriented to spray in a direction substantially toward any other second active spray nozzle, and the three or more second active spray nozzles oriented to spray in a direction towards the location for a user in the booth, and wherein the second active spray nozzles are operable to spray tanning composition only when offset from the first arm. In a preferred design of this aspect of the invention, the second arm is positioned on the opposite side of the location for a user from said first arm.

In another aspect of the preferred design of the invention, an apparatus is provided for applying an artificial tanning composition to a human user without overly darkening the user's feet, the apparatus comprising a booth suitable for containing a user's torso, legs and feet; a foot rinser near the bottom of the booth; and a coating sprayer above the bottom of the booth containing an artificial tanning composition including an artificial tanning agent for spraying portions of said user's torso and legs, and operable while said foot rinser is in use.

In a preferred design, the foot rinser has one or more rinse nozzles mounted to the booth and connected to a pressurized source of foot rinser solution to rinse the feet of a person standing in the booth. In one preferred design, the foot rinser rinses the feet for at least the time period during which the coating sprayer sprays tanning composition.

In yet another aspect of the preferred design, the apparatus includes an input device for inputting or measuring a user's height, and the coating sprayer traverses to an upper height about equal to the input or measured height. In one alternative, the upper height can be entered by an operator with a keypad or other input device. As another alternative, the apparatus has a photo-optic sensor, ultrasonic sensor, or other object sensor or intelligent vision device, which, for examples, may be either mounted to the arm or to the booth, such that the sensor will measure the height of the person standing in the booth. The sensors are coupled to the coating sprayer drive control to limit the upper height traversed by the arm.

Yet another aspect of a preferred design of the present invention provides for An apparatus for differentially applying a composition to a human body comprising an applicator for spray applying a first liquid containing a certain non-zero concentration of an active agent to one part of a body and for spray applying a second liquid having a different concentration of said active agent to a different part of the body. In a one embodiment, the applicator uses different nozzles for the first and second liquids. In a preferred embodiment, the nozzles for the first and second liquids can operate simultaneously. In a further preferred embodiment, at least one nozzle for the second liquid operates substantially the entire time the nozzles for the first liquid operate. As examples, the second liquid can have an active agent concentration of zero and the active agent may be an artificial tanning agent. As another example, the second liquid may have a lower, non-zero concentration of active agent and may be applied to areas of the body more sensitive to the activity of the active agent, thereby obtaining a more uniform response to the agent's activity over all areas of a user's skin upon coating.

In yet another aspect of the preferred design, the apparatus is provided with a washdown nozzle mounted to the spray booth and coupled to a source of sanitizing solution to wash the spray booth enclosing walls and floor. The washdown nozzle or nozzles are preferably rotating, tank washing type nozzles.

Related objects and advantages of the present invention will be apparent from the following figures and description of the preferred embodiments.

DESCRIPTION OF THE PREFERRED EMBODIMENTS

Figure 1:
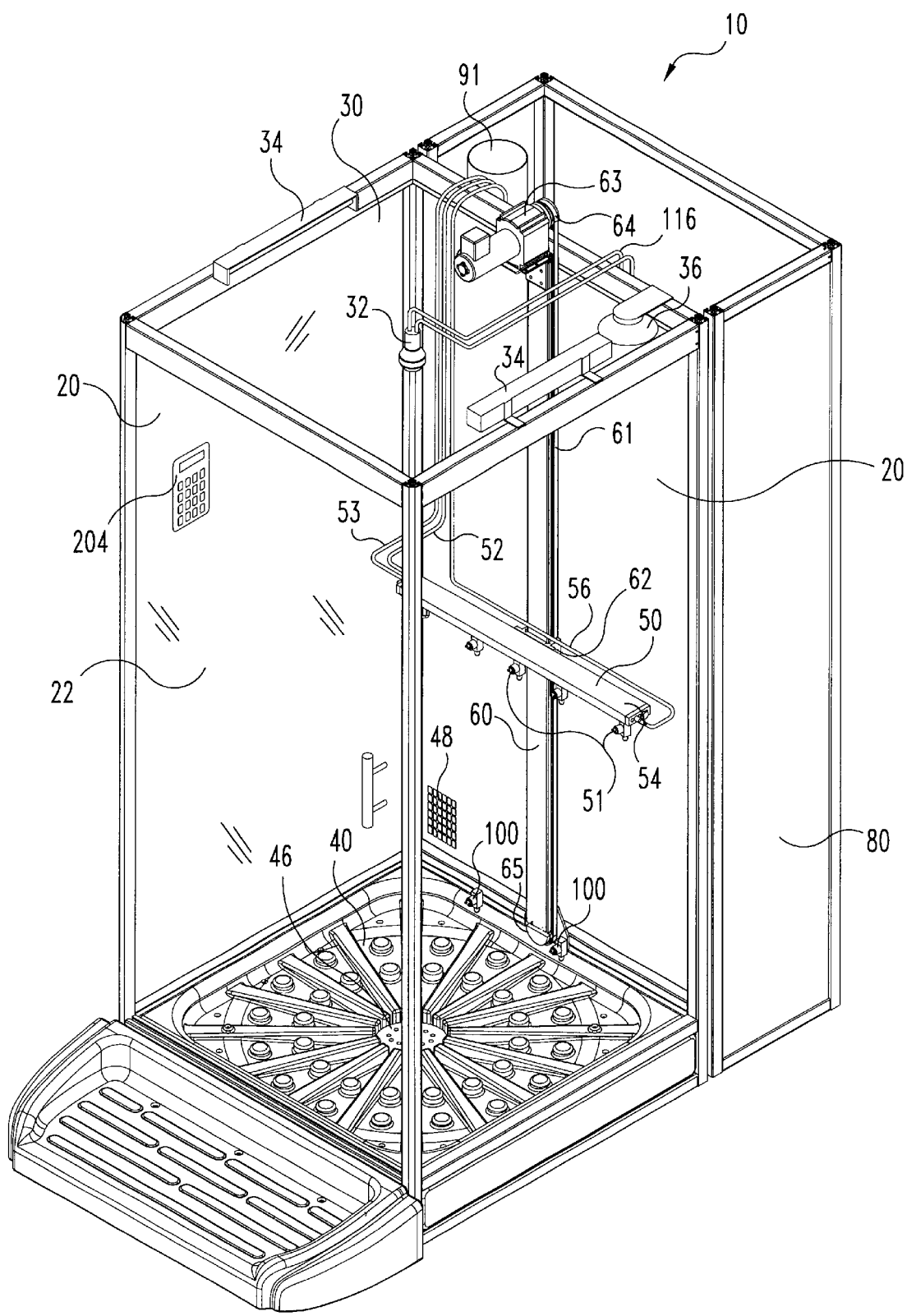
FIG. 1 shows one design for a spray apparatus of the present invention adapted for use in a spray booth for coating a person with tanning composition.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated apparatus, and such further applications of the principles of the invention as illustrated therein being contemplated as would normally occur to one skilled in the art to which the invention relates.

As used herein, the term "tanning composition" means any composition designed for application to the skin to facilitate the cosmetic coloring of the skin to achieve a tanned appearance. The term includes, but is not limited to, sun tanning solutions, oils and creams, as well as compositions which stain or induce a change in pigmentation of the skin. Tanning compositions may also be blended with other components such as moisturizers, vitamins, surfactants, emulsifiers, solvents, extenders, therapeutic skin agents, etc.

As used herein, the term "artificial tanning composition" means a tanning composition that does not rely on UV radiation, either from sunlight or from UV generating light bulbs, to cosmetically color the skin. The term includes within its meaning, but is not limited to, "sunless tanning" and/or "bronzing" solutions, oils, and creams, as for example, but without limitation, compositions containing the artificial tanning active agents such as dihydroxyacetone, erythrulose, lawsone, orjugulone. Artificial tanning compositions may contain one or more active artificial tanning agents and may be blended with sun or UV tanning facilitators, as well as moisturizers, vitamins, surfactants like ethoxydiglycol and dimethyl isosorbide, emulsifiers, solvents, thinners, extenders, dyes, fragrances, therapeutic skin agents, etc.

As used herein, an "operator" is a person who operates the controls of an apparatus of the present invention or who maintains the apparatus in operational condition.

As used herein, a "user" is a person who is to be coated, is being coated, or who has been coated by the apparatus or methods of the present invention.

Though the apparatus of the present invention is primarily designed to provide optimum benefit in the application of artificial tanning compositions, it is to be understood that the apparatus can also be used to coat a human body with other liquids for cosmetic or therapeutic purposes, as for example, but without limitation, sun tanning compositions for use in outdoor or indoor UV based tanning, sunscreen compositions, insect repellants, general skin care compositions, and pharmaceutical compositions for adsorption through the skin or for topical treatment of the skin, such as applying cortisone for psoriasis.

Referring now to FIG. 1, one aspect of the present invention provides for a spray booth apparatus for applying a tanning composition to a human body. A spray apparatus is adapted to operate within a booth 10 having enclosing walls 20, a door 22, a ceiling 30, and a floor 40. The booth may be of any convenient form provided the spray apparatus is supported, and preferably such that the booth provides containment for the spray to protect the surrounding area from over-spray if desired. For more convenience, the figures show booths having basic rectangular box shapes, though it is to be understood that cylindrical, oval, or irregularly shaped booths, etc., may also be suitable as desired.

The booth may be constructed of any convenient material to provide structural stability and resistance to water and staining by the tanning composition as, for example but without limitation, plexiglass, fiberglass, shatter resistant glass with metal framing, stainless steel, plastic, and the like. If containment of the over-spray is of lesser concern in certain applications, and the spray apparatus is otherwise supported, the booth may even comprise simple shower type curtains or no enclosing walls or doors at all.

The booth may optionally be provided with lights and/or speakers for the comfort and convenience of a user. As for example, but without limitation, speakers may be mounted to the booth to provide background music, and/or playback of recorded instructions to step a user through an application session. FIG. 1 shows lights 34 and a speaker 36 mounted in ceiling 30, advantageously away from direct impact of tanning composition or sanitizing solution spray. With appropriate protective devices, lights and speakers may also be suitably mounted in the walls 20, door 22, or floor 40 as desired.

The booth floor 40 is provided with at least one drain 46 and may take any suitable form to provide a supporting surface for a user standing in the booth, such that excess fluid may freely drain away from the feet of the user. One non-limiting example of a suitable floor is a molded floor with at least one drain and recessed channels leading from all regions of the floor to the drain or drains, with the channels being narrow enough and deep enough for a user to comfortably stand on the floor without waste fluid in the channels contacting the user's feet. Another non-limiting example of a suitable floor is a floor having a grate to support a user standing thereon, with a fluid collection reservoir under the grate with at least one drain therein. Other suitable floors will be apparent to one skilled in the art, which provide adequate support for a user to stand thereon, while providing sufficient drainage to minimize retention of excess fluid in contact with the user's feet.

Figure 2:
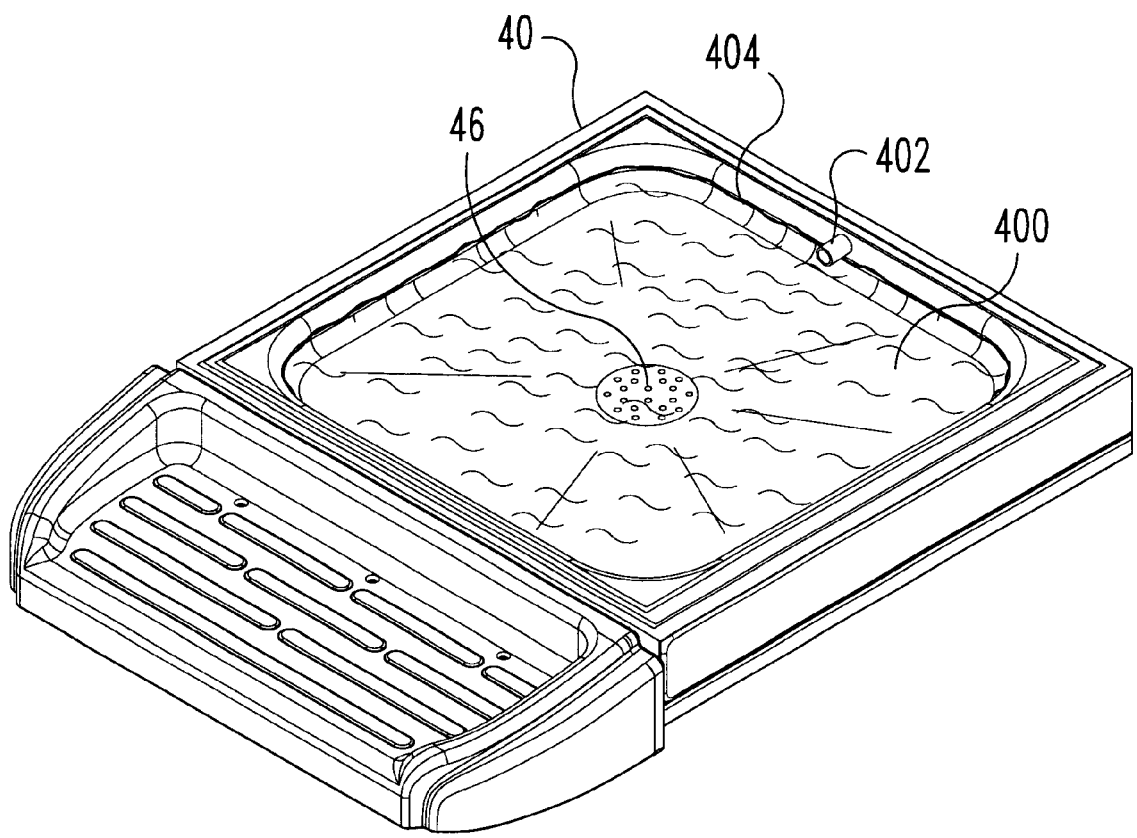
FIG. 2 shows an alternative design for a floor for a spray booth apparatus according to the present invention, having a foot rinser comprising a foot bath.

In an alternative design, one embodiment of which is illustrated in FIG. 2, the floor may comprise a foot rinser as discussed below, including a reservoir 400 for foot rinser solution in the form of a foot bath, filler nozzles 402, and at least one drain 46. In this alternative design, a user stands in the foot bath, which is preferably filled with foot rinser solution 404, preferably for at least the period during which the user is being sprayed with tanning composition.

Referring now to FIGS. 1 and 3–10, an arm 50 is movably mounted in the booth 10 so as to traverse within the booth 10 in relation to a user standing in the booth 10. The arm 50 has three or more active nozzles 51 such that none of the active nozzles are oriented to spray in a direction substantially toward any other active spray nozzle. Though there may be other nozzles for spraying tanning or other compositions in the booth, nozzles for spraying tanning composition are preferably only active when they will not spray in a direction substantially toward any other active spray nozzle. In this manner, opposing air flows are avoided which may cause swirling or eddying of spray-laden currents around the body to be coated, rather than the even deposition of the spray on the body. Likewise, excessive air currents are to be avoided, as for example, but without limitation, by directing the spray of tanning composition into a secondary air current which passes the body to be coated. Such excessive air currents tend to perturb the even spray of tanning composition such that a substantial proportion of the spray flows around and away from the body, rather than being deposited on the body. In addition to reducing the efficiency of deposition of tanning composition on the body being coated, these types of perturbations caused by excessive air flows and opposing air flows tend to cause substantial coalescence of droplets in the spray, increasing the range of droplet sizes in the spray and the maximum droplet size in the spray, resulting in uneven application and dripping or streaking of the coating of tanning composition on the body.

Figure 3:
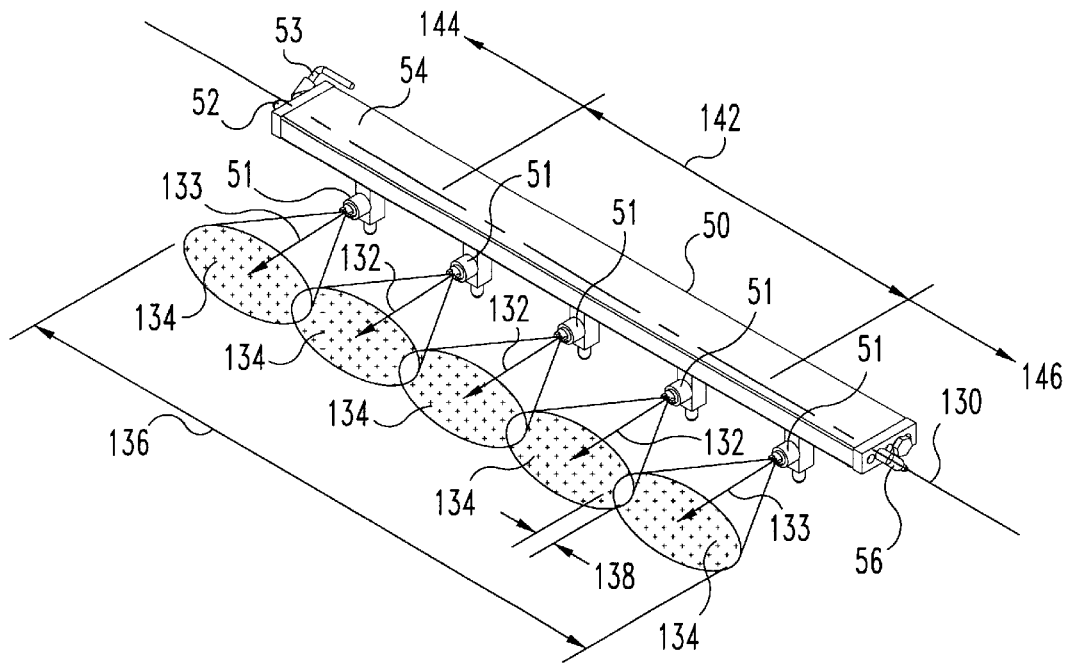
FIG. 3 is a perspective view of one design for a movable arm with a plurality of nozzles showing one geometric relationship of the spray directions.

In one preferred design illustrated in FIG. 3, the arm 50 has opposing ends and defines an axis 130, outer portions 144 and 146 adjacent the opposing ends, and a central portion 142 between the outer portions. A plurality of spray nozzles 51 are on the arm 50, wherein at least one spray nozzle 51 is on the central portion 142 and at least one spray nozzle 51 is on each of the two outer portions 144 and 146. Each spray nozzle on the central portion 142 defines a spray direction 132 towards a certain location in the booth 10, said location being the location for positioning a user during use, also referred to as the predetermined location. Each spray nozzle on an outer portion 144 or 146 defines a spray direction 133 towards the certain location in the booth 10.

In one embodiment of the invention, as illustrated in FIG. 3, the spray directions 132 and 133 of all the spray nozzles 51 are parallel to one another. The spray directions may, for example, be substantially horizontal relative to the booth 10 and perpendicular to the general axis 130 of arm 50. They may alternatively be at any other convenient angle relative to the booth 10 and arm 50 as desired, given they are directed toward the predetermined location within the booth 10 and preferably no spray direction of an actively spraying nozzle is oriented in a direction substantially toward any other actively spraying nozzle's spray direction.

Figure 4:
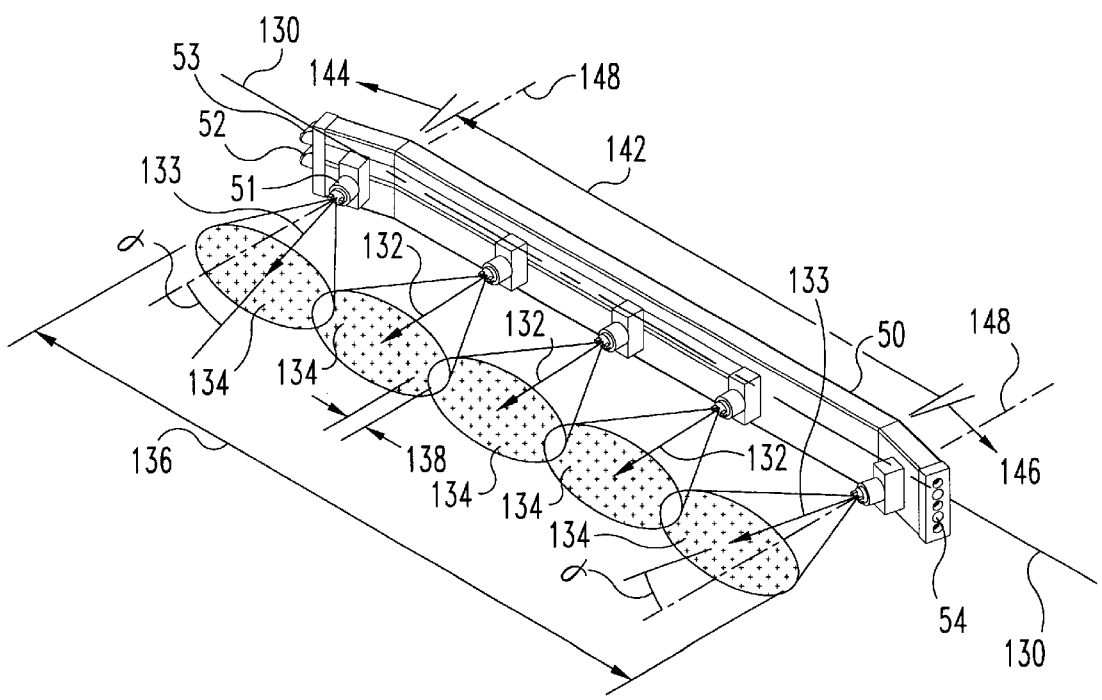
FIG. 4 is a perspective view of another design of a movable arm with a plurality of nozzles showing an alternative geometric relationship of the spray directions.
Figure 5:
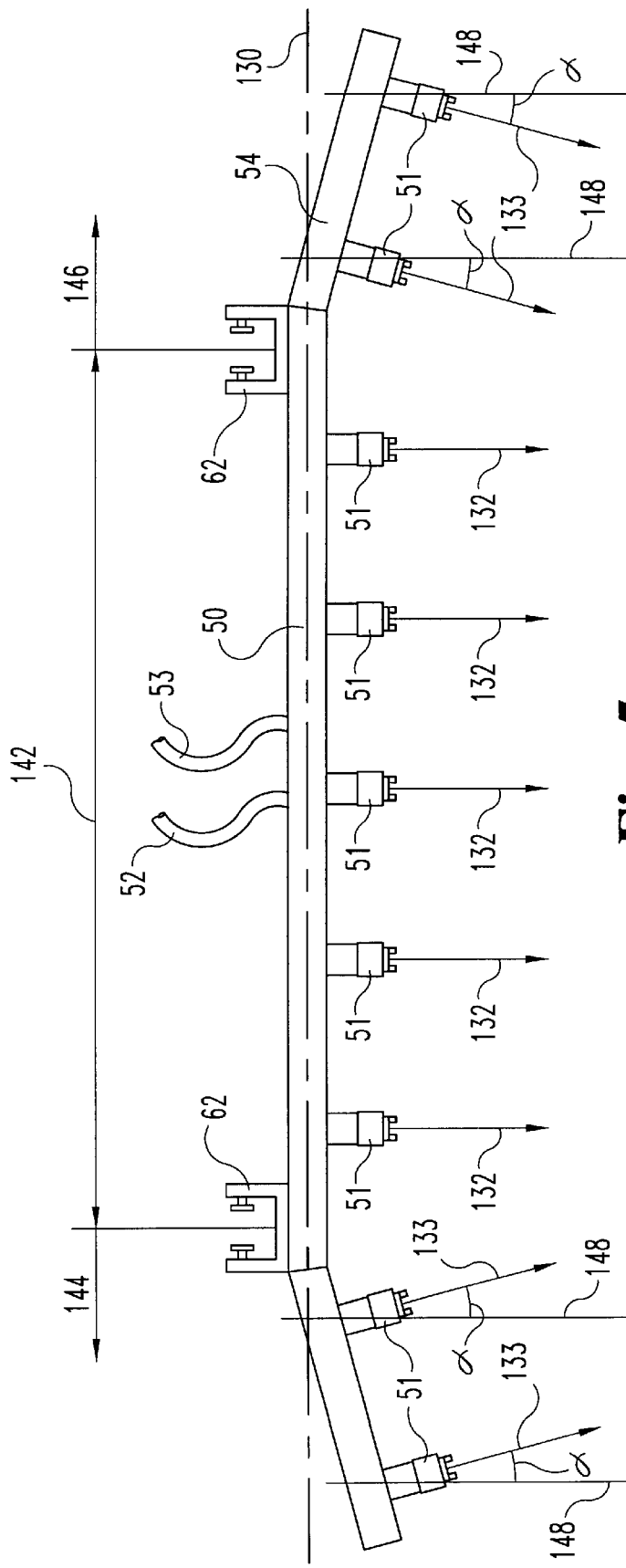
FIGS. 5 and 6 are side views of additional embodiments of a movable arm with a plurality of spray nozzles.
Figure 6:
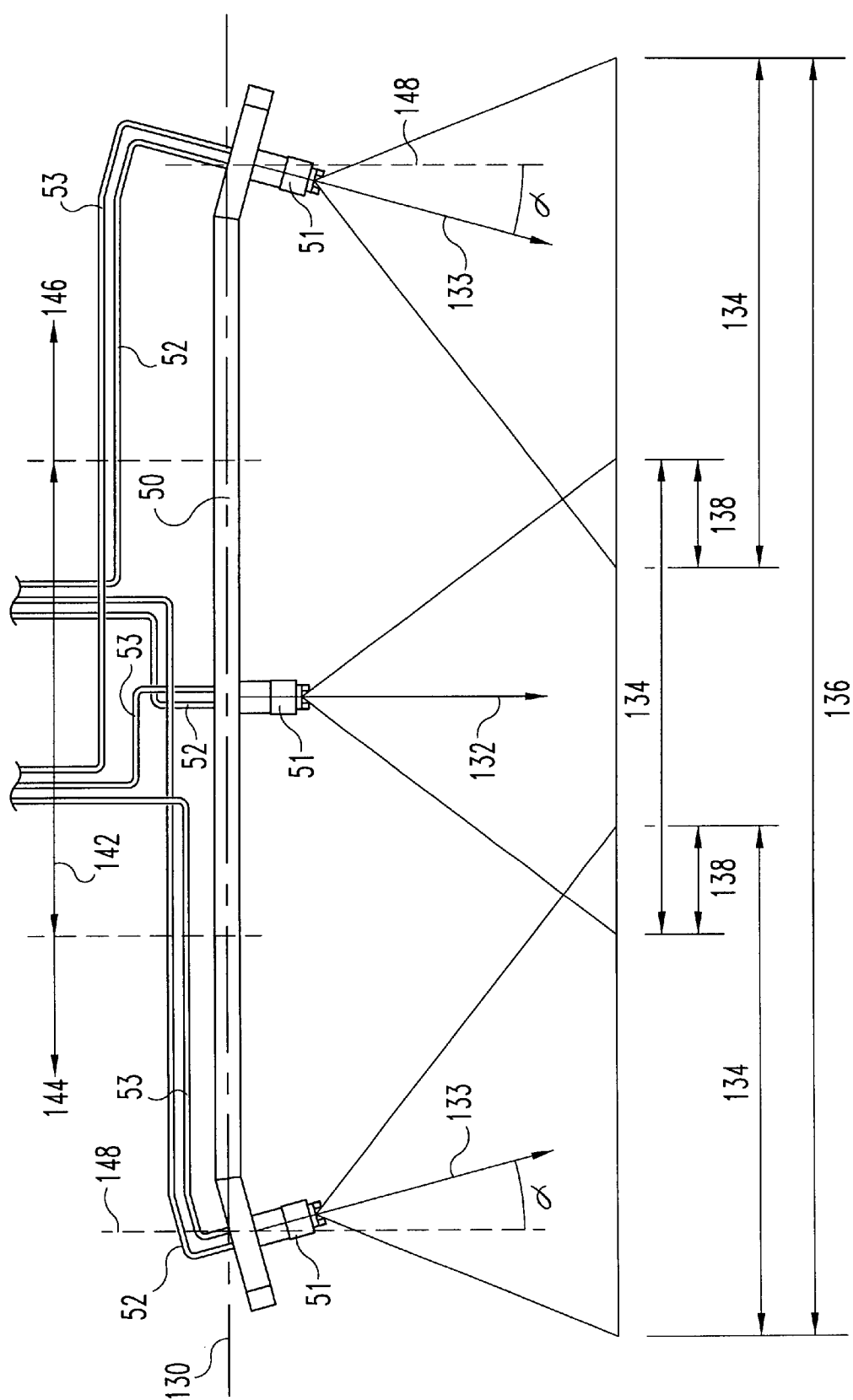

In a preferred embodiment, as illustrated in FIGS. 4–6, the spray directions 132 of all the spray nozzles 51 on the central portion 142 of the arm 50 are parallel to one another, and the spray directions 133 of all the spray nozzles 51 on either outer portion 144 or 146 of arm 50 are parallel to the spray directions 133 of nozzles 51 on the same outer portion 144 or 146, and the spray directions 133 of all the spray nozzles 51 on each of the outer portions 144 and 146 are directed towards the certain location in the booth 10 at an angle α, which is between about 0 and about 20 degrees, preferably between about 10 and about 20 degrees, most preferably about 15 degrees, from a line 148 parallel to the spray directions 132 of the spray nozzles 51 mounted on the central portion 142 of the arm 50. The spray direction of a nozzle shall be considered the direction of the center of mass of the fluid being sprayed from the nozzle. By having the nozzles 51 on the outer portions 144 and 146 be inwardly, that is convergingly, directed toward the certain location in the booth, the resulting spray may provide a more even coating to the sides of the torso, legs and arms of a user, as well as the insides of the legs and arms. By limiting the angle of convergence to no more than about 20°, preferably about 15°, the spray directions are not substantially directed toward the spray directions of nozzles on the central portion 142 of arm 50 so as to perturb the even spray deposition of tanning composition on a user.

Again, the spray directions 132 and 133 may, for example, be substantially horizontal with spray directions 132 substantially perpendicular to the arm 50. However, alternative suitable designs may be desirable for design considerations, such that any convenient angle for spray directions 132 and 133 relative to the booth 10 and arm 50 may be used, provided they are directed toward the predetermined location within the booth, and the relative spray direction geometries are maintained as described.

As illustrated in FIGS. 3 and 4, each nozzle 51 produces a spray pattern 134 at the certain location for a user in the booth 10. In a preferred embodiment, the spray pattern 134 is fan shaped with a larger dimension along the line parallel to axis 130 than the dimension perpendicular to axis 130. In another preferred embodiment, the spray patterns 134 are aligned to provide an overlap 138 with adjacent spray patterns 134 of at least about 5%, preferably at least about 10% at the predetermined location in the booth 10.

The spray patterns 134 of all the nozzles 51 combine to provide a combined spray pattern 136. In one preferred embodiment, wherein the arm 50 is substantially horizontal and traverses vertically within the booth 10, the combined spray pattern 136 has a horizontal width of between about 70 cm and about 100 cm at the predetermined location in the booth 10, which is sufficiently wide to relatively evenly coat the bodies of users corresponding to about 95% of the population, when standing at the predetermined location in the booth 10, based on statistical widths of human beings.

In another preferred embodiment, wherein the arm 50 is mounted in a substantially vertical orientation, the vertical width of the combined spray pattern 136 corresponds to the vertical dimension of the portion of the body to be coated. In one embodiment, the vertical width of combined spray pattern 136 corresponds to substantially the height of a body being coated. In a preferred embodiment, the vertical width is at least about 190 cm. In another preferred design, the vertical width is adjustable to correspond to the input or measured height of a user.

In operation, the plurality of spray nozzles 51 produce a spray optimized to provide a relatively even coating on the skin of a user, with substantially no streaking or dripping. It has been surprisingly found that this can be accomplished by regulating the spray patterns and spray direction geometries of the nozzles, as well as the average droplet particle size, the nozzle liquid and air feed pressures, the viscosity of the tanning composition, and the volume of tanning composition sprayed per area of user skin, which may be controlled by regulating the volume of tanning composition sprayed per distance traversed by the arm 50.

Figure 9:
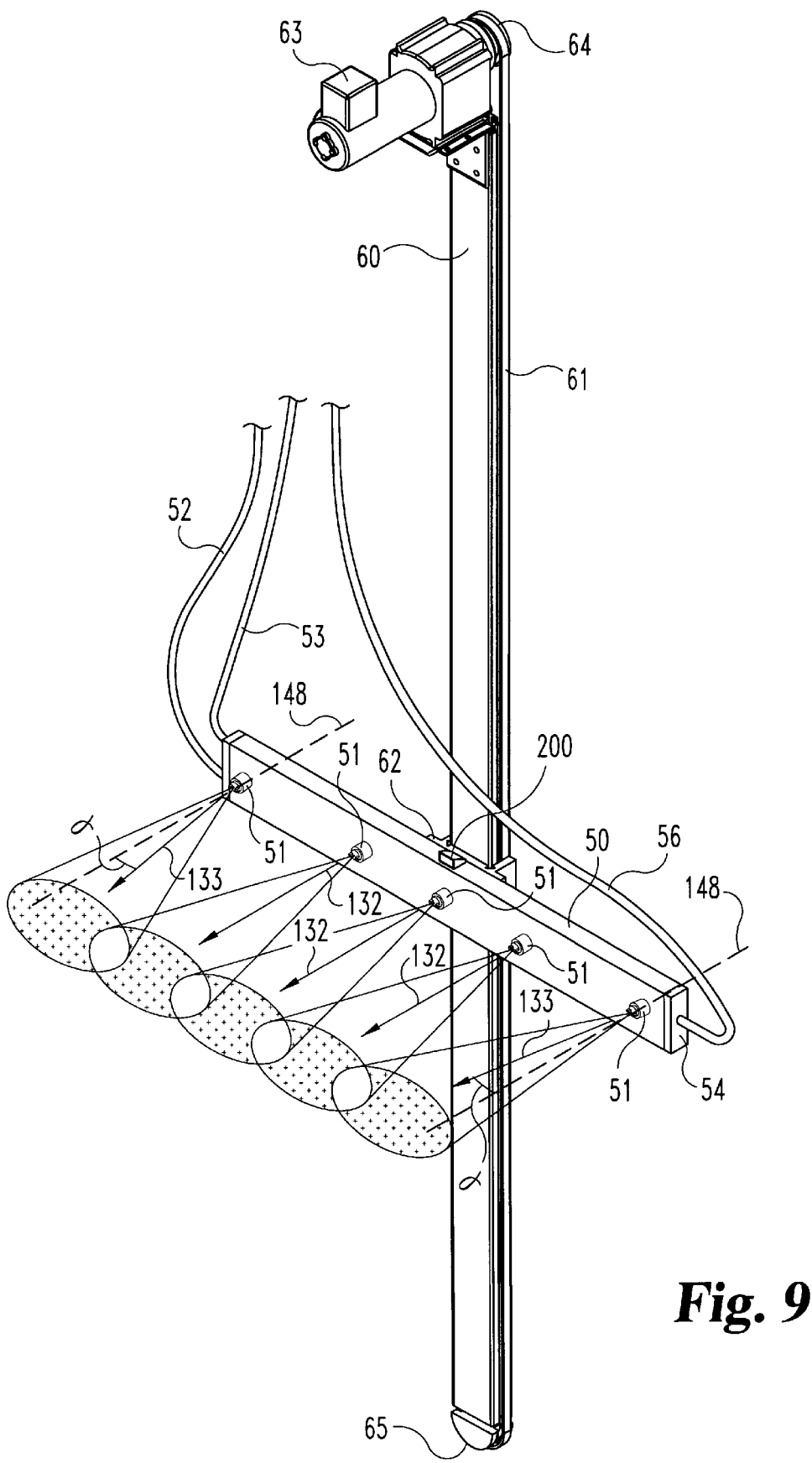
FIG. 9 shows another embodiment of a spray arm on a gantry type drive system.

In a preferred embodiment, nozzles 51 produce a spray having a volume median diameter (VMD or $Dv_{0.5}$) of not greater than about 200 μm, preferably not greater than about 100 μm. Due to the present limitations on hydraulic atomization nozzles and the above preferences on spray characterization, air atomization nozzles are preferred, though hydraulic nozzles capable of producing sprays with VMD's not greater than about 200 μm, preferably not greater than about 100 μm may be suitable. One specific example of a suitable nozzle and operating conditions, without limitation, is the external mix, flat spray, air atomizing 1/8J with a SUE 18B Spray set-up available from Spraying Systems Co., Wheaton Ill., operating at a liquid pressure of about 5 to about 20 psi (about 35–140 kPa), preferably about 10 psi (about 70 kPa) and air pressures in the range of about 15 to about 30 psi (about 100 to about 200 kPa).

In another preferred embodiment, the plurality of nozzles 51 are configured to spray between about 0.30 mL and about 0.45 mL, preferably between about 0.30 mL and about 0.38 mL, tanning composition per vertical centimeter traversed by arm 10 when traversal is in the vertical direction.

The preferred viscosity of the tanning solution is approximately that of water (about 1 centipoise), preferably less than about 30 centipoise, though viscosities up to about 100 centipoise may also be suitable.

A predetermined location within the booth is provided for a user to stand during a tanning composition application operation according to the present invention. It is generally convenient for the location to be in the central portion of the booth 10 though alternatives may be suitable for design considerations, as for example, the back, side or front of the booth relative to the arm. In one embodiment, the predetermined location is in front of the spray nozzles and is at a horizontal distance of between about 25 cm and 60 cm, measuring to the surface of the user's body closest to the nozzles. Greater or lesser distances can be used by adjusting the nozzle liquid and air feed pressures accordingly, as for example by increasing the feed pressures for greater distances. Greater distances, however, may lead to greater spray pattern dispersion and more combining of spray droplets, resulting in a sub-population of less desirable large droplets, which may drip or streak after deposition on the skin or result in an uneven coating.

In one specific preferred embodiment, the arm is mounted substantially horizontally within the booth to traverse in the vertical direction, with the predetermined location in the booth 10 being between about 25 cm and about 60 cm horizontal distance from the nozzles 51, with the spray patterns 134 overlapping adjacent spray patterns 134 by at least about 10%, and the plurality of nozzles 51 being configured to spray between about 0.30 mL and about 0.38 mL tanning composition per vertical centimeter traversed by the arm 10, with a VMD of not greater than about 100 μm, sprayed from an air atomizing nozzle with a liquid feed pressure or about 10 psi and an air feed pressure of about 10–30 psi.

It is to be understood that the arm 50 can be of any form desired to produce the desired orientation of spray patterns 134 generated by the nozzles 51. FIG. 9 shows one embodiment of an arm 50, wherein the arm is a manifold 54 having the plurality of nozzles 51 mounted into the broader, vertical face of the rectangle. The manifold 54 is a two compartment bar providing pressurized feed of tanning composition through tanning composition feed line 52 into one compartment, and pressurized feed of air through compressed air feed line 53 into the second compartment. In this manner, each nozzle 51 receives equivalent feeds of air and liquid which is then atomized into a spray in the nozzle 51. Optionally, manifold 54 may be fitted with a tanning composition return line 56 to drain residual composition to the reservoir or drain as desired.

FIGS. 4 and 5 show other embodiments wherein the arm 50 is a manifold 54 and is bent at the outer portions 144 and 146 relative to the horizontal axis 130 of the central portion 142 of the arm 50 to provide convergent angled spray directions 133 for nozzles 51 mounted to the outer portions 144 and 146 of the arm 50. Feed lines 52 and 53 provide pressurized feed of tanning solution and air respectively, to the two compartment manifold 54, which then supplies each nozzle 51 equivalently. Again, the manifold may be optionally fitted with a composition return line desired (not shown).

FIG. 6 shows yet another embodiment for arm 50, wherein the arm is a simple mounting bar to which the plurality of nozzles 51 is attached. In this embodiment, each nozzle 51 is supplied with individual pressurized feed lines 52 and 53 for tanning composition and air, respectively.

FIGS. 1, 3 and 9 show a preferred embodiment for arm 50, wherein the arm 50 includes a two compartment manifold 54, wherein the nozzles 51 are mounted to the broader face of the arm 50, but the arm 50 is oriented with the broader face being horizontal, rather than vertical. Having the nozzles 51 suspended under the arm 50 advantageously allows for a lower effective vertical traversal of the arm 50, as well as allowing for the angular setting of the nozzles 51 on the outer portions 144 and 146 to be more easily installed or adjusted. Nozzles 51 may be suitably mounted on the top surface of the arm as well.

FIGS. 7 and 8 show alternative designs for a spray apparatus according to the present invention, wherein the arm 50 is mounted substantially vertically to traverse either substantially horizontally along one or more substantially horizontal tracks 300, as for example as illustrated in FIG. 7, or along a tracks 302 completely or partially around the predetermined location in the booth, as for example as illustrated in FIG. 8. The track 302, illustrated as a partial ellipse in FIG. 8, may be of any convenient shape to partially or completely encompass the predetermined location, and therefor a user standing in the predetermined location. Such shapes can include, but are not limited to a circle, ellipse, oval, square, rectangle, grouping of arcs, other irregular shape or the like, or any portion of such shapes. In designs using a substantially horizontally mounted arm, it is preferred to have the spray directions of all the nozzles be substantially parallel one to another, and with overlaps between adjacent spray patterns at the predetermined location of at least 10%.

Other suitable designs for arm 50 will be apparent to one skilled in the art, including esthetically pleasing designs, such as curved arms or stylized arms. These are suitable provided the geometry of the spray directions 132 and 133 are maintained as described above. Likewise, arm 50 may be oriented at angles other than substantially horizontally or vertically, such as a helically traversing arm, with the spray geometries not substantially opposing one another.

A number of drive means are suitable to drive and control the traversal of the arm. Suitable means will provide arm traversal coupled to the spray rate to achieve the desired delivery rate of tanning composition to the user's skin. In one embodiment, the drive means provides consistent, smooth traversal at a predetermined rate to coincide with the spray rate of nozzles 51, to provide for the application of a controlled volume of tanning composition per surface area of a user's skin. Exemplary drive means include without limitation, gantries with a motor driven belt or chain to move the arm, hydraulic or pneumatic piston drives, and motors with drive gears mounted to the booth or alternatively to the arm, coupled to gear tracks to move the arm.

FIGS. 1 and 9 illustrate one suitable embodiment of a drive mechanism comprising arm 50 mounted to bearing bracket 62, which is configured to moveably mount on vertical guide rail 60. Belt 61 is attached to bearing bracket 62 and is driven by motor 63 through drive gear 64 to move arm 50 along guide rail 60 in coordination with the turning of belt 61. In one embodiment, belt tensor 65 maintains proper belt tension for smooth traversal motion of arm 50. In a preferred embodiment, belt 61 is ribbed to provide greater precision of motion of arm 50. In another preferred embodiment, belt 61 is replaced with a chain. Other drives will be apparent to those skilled in the art, including for example, replacing the above gantry with an hydraulic or pneumatic piston, as for example a fluid or air driven telescoping post on which arm 50 would be mounted.

In one design of the present invention, the arm traverses vertically between a lower height and an upper height selected to provide for coating of all or any desired portion of a person desiring to be coated. In a preferred embodiment, the arm traverses to coat the entire body of a user. In another embodiment, the lower height is selected to be at about the height of the top of a user's feet and the upper height is selected to be at least equal to about the height of a user. In yet another embodiment, the arm is configured to traverse between a lower height of between about 7 cm and about 18 cm, and an upper height of at least about 190 cm, the heights being measured from the floor of the booth.

Figure 7:
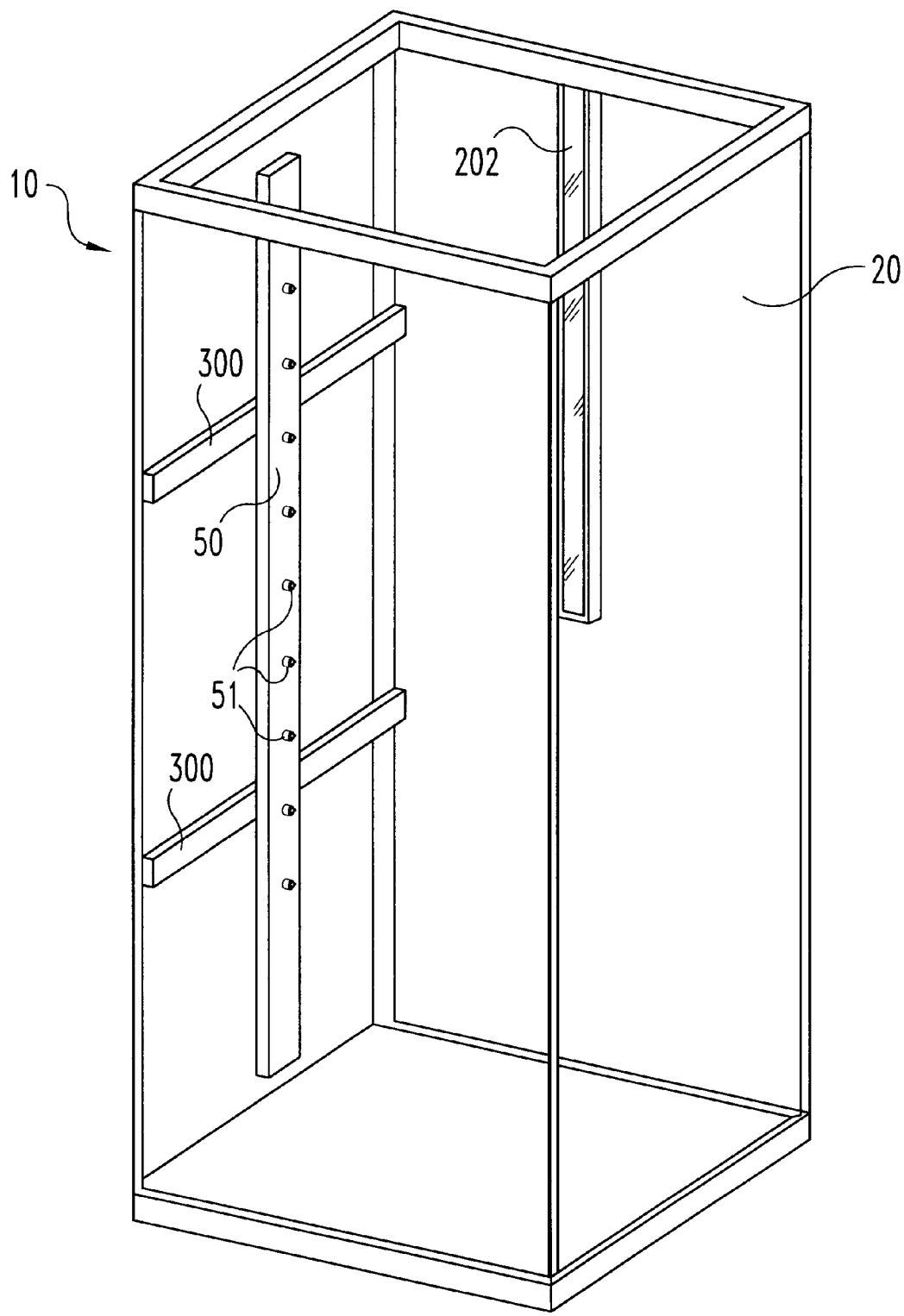
FIG. 7 is a perspective drawing of another design for a spray booth according to the present invention with a horizontally traversing arm.
Figure 8:
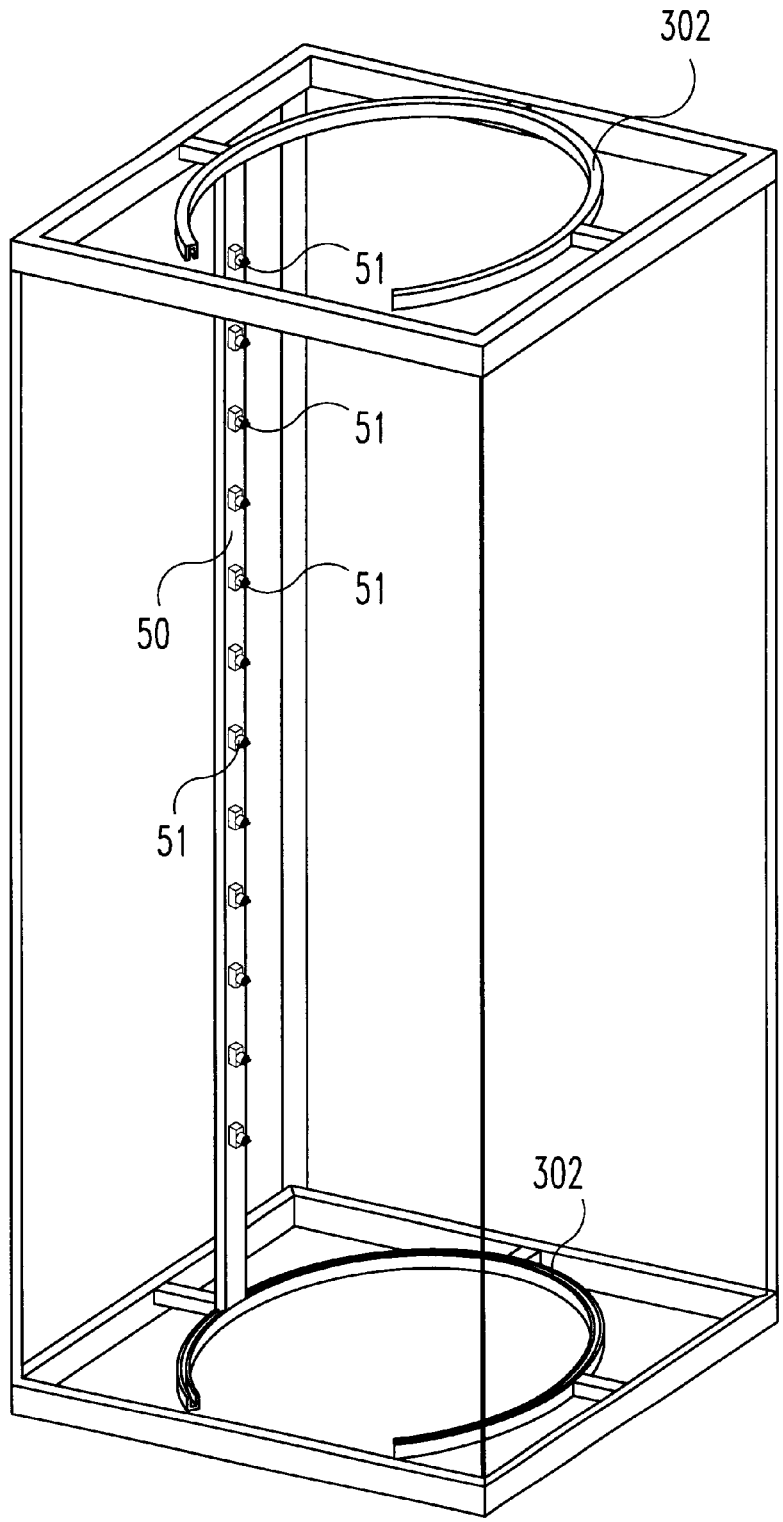
FIG. 8 is a perspective drawing of another design for a spray booth according to the present invention with a vertical arm having multiple spray nozzles, movably mounted to the booth to traverse in an approximately elliptical path around a location for a user to stand within the booth.

In another embodiment of the present invention, there is provided an input device mounted to the booth to input the height of a person standing at the predetermined location in the booth. The input device then coordinates the traversing of the arm to limit the upper height to a height equal to about the input height. In one embodiment, illustrated in FIG. 1, the input device is a keypad 204 mounted inside the booth for an operator or a user to key in the desired upper height. Alternatively, keypad 204 may be mounted outside the booth or may be located at a remote control station. In another embodiment, the input device is a height sensor mounted in the booth to measure the height of a user, as for example, but without limitation, a photo-optic, ultrasonic, or infrared sensor. FIG. 9 illustrates one such embodiment, wherein height sensor 200 is mounted to the arm 50. FIG. 7 illustrates an alternative embodiment, wherein an array of height sensors 202 is mounted to the enclosing walls 20 of the booth 10 to measure the height of a user. In designs using vertically mounted arms, the height input device may be couple to the sprayer to allow activation of spray nozzles only up to the input (measured) height, with higher mounted nozzles remaining inactive during the subsequent coating application. Alternatively, the nozzles may be manually or automatically movable along arm 50 to proportionately adjust the heights of the nozzles. Additionally in this embodiment, the nozzles may optionally be focusable to adjust the spray patterns to optimize the overlap between adjacent spray patterns to optimize the spray for users of different heights.

In another aspect of the present invention, the spray apparatus further comprises a second arm moveably mounted in the booth with three or more second active spray nozzles on the second arm oriented as described above for the first set of three or more nozzles on the first arm, wherein the three or more second spray nozzles are operable when they are offset from the first arm. In one embodiment, the horizontal distance between the predetermined location and the second spray nozzles is between about 25 cm and about 60 cm, though other distances may be used by adjusting the spray pressure accordingly, as with the first spray nozzles on the first arm.

The offset, or stagger distance, between the arms is such that the spray from the active nozzles on the first arm and the spray from the active nozzles on the second arm do not interfere with one another to any appreciable extent. In this manner, two or more moveable spray arms can be employed in the apparatus to more rapidly coat a user without creating adverse opposing air flows or excessive air flows as described above.

In one preferred embodiment, the offset, or stagger distance, is equal to or greater than about the sum of the widths in the direction of arm traversal of the spray patterns of the first spray nozzles on the first arm and the second spray nozzles on the second arm. In another embodiment, the offset is equal to or greater than about two times the sum of the widths of the spray patterns of the first and second sets of spray nozzles measured in the direction of traversal.

Figure 10:
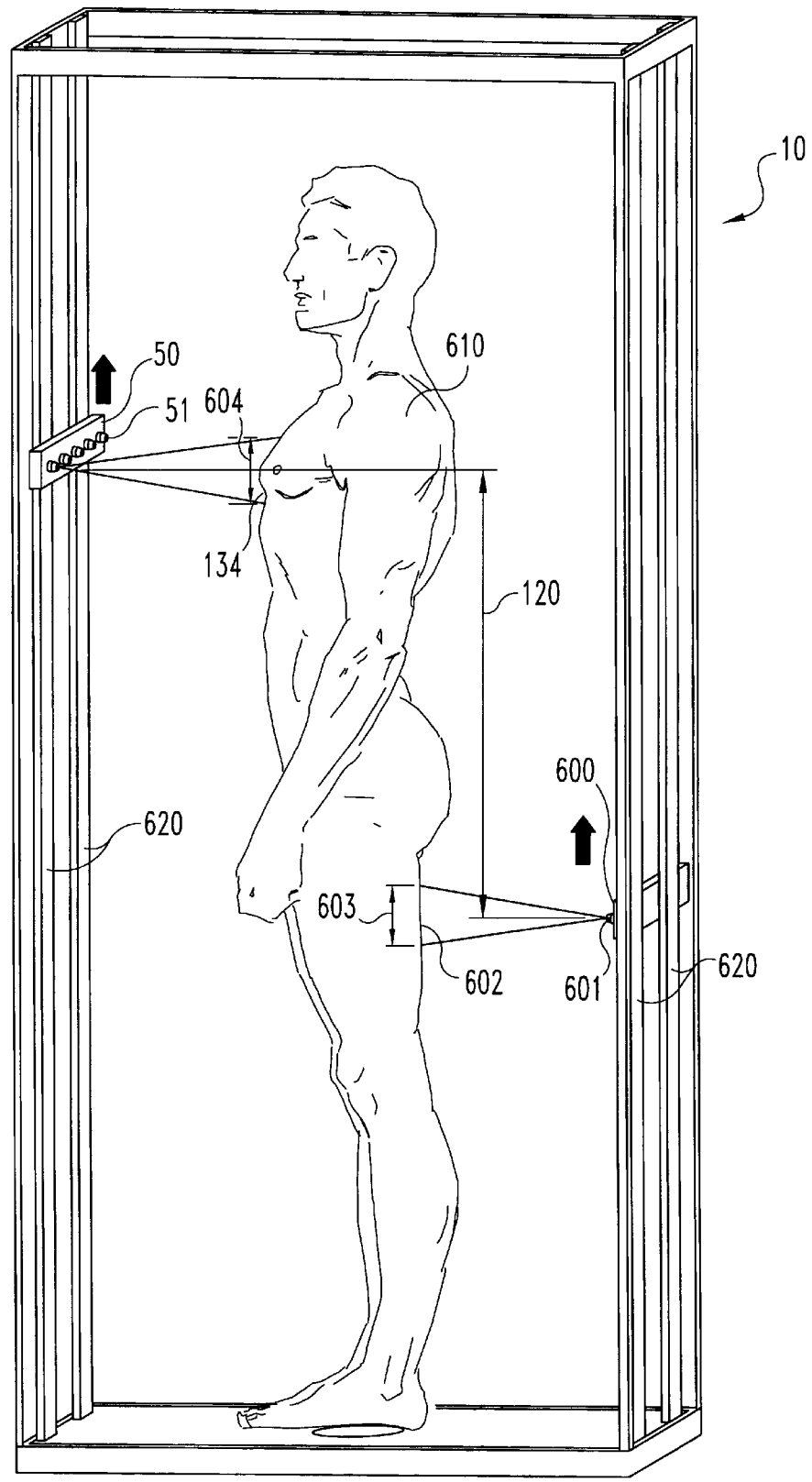
FIG. 10 is a perspective view of a spray booth according to the present invention having two arms, each with a plurality of spray nozzles, vertically traversing with a vertical stagger distance between them.

One design for an apparatus with two spray arms is illustrated in FIG. 10. Second arm 600, having second spray nozzles 601 thereon, is positioned on the opposite side of the booth 10 from the first arm 50. This is also advantageously on the opposite side of the location for a user 610 from the first arm 50. The design shown in FIG. 10 shows the first arm 50 and second arm 600 traversing vertically along vertical guide tracks 620, separated by a vertical stagger distance 120, which is sufficient to avoid appreciable opposing flows that would perturb the spray patterns of the nozzles. In one embodiment, the vertical stagger distance 120 is at least about the sum of the vertical widths 603 and 604 of first spray pattern 134 and second spray pattern 602, respectively. In another embodiment, the stagger distance 120 is at least about two times the sum of the vertical widths 603 and 604.

It is to be understood that the stagger distance between the first and second arm is measured in the direction of traversal of the arms, whether traversal is vertical, horizontal or otherwise. If the arms are traversing in opposing directions, the nozzles of one arm should stop spraying when the arms come to within the necessary minimum stagger distance, and may resume spraying after the lead arm has passed and re-established the minimum stagger distance from the paused nozzles.

In another aspect of the present invention, there is provided a spray apparatus for applying an artificial tanning composition to a human body including a foot rinse system to rinse the feet of the user during the application of tanning composition. The foot rinser operates to reduce or minimize as desired, contact of the tanning composition with the feet, particularly the soles, between the toes, and toe nails, of a user to minimize or eliminate undesirable over-staining of the feet. In one embodiment, the foot rinser comprises at least one rinse nozzle operably mounted to the booth and operably connected to a source of foot rinser solution, to rinse the feet of a user positioned at the predetermined location in the booth. The foot rinser preferably rinses the user's feet for at least the period of time during the spraying of the tanning composition. In a preferred embodiment, the foot rinser begins rinsing just prior to the beginning of spraying of the tanning composition. In another preferred embodiment, the foot rinser continues rinsing for at least until after the over-spray has settled or the user has exited the booth.

One design for the foot rinser, comprising at least one foot rinse nozzle mounted to the booth and oriented to direct a stream of foot rinser solution across a user's feet when said user is standing at the predetermined location, to dilute tanning composition over-spray that falls on the feet. In a preferred embodiment, the stream of foot rinser solution is sufficient to dilute the over-spray such that no appreciable concentration of artificial tanning agent adheres to the user's feet.

FIG. 1 illustrates one design for a foot rinser having two foot rinse nozzles 100 attached to booth 10 at one edge of floor 40. However, many suitable alternative designs will be readily apparent including, without limitation, mounting one or more nozzles opposite those shown in FIG. 1 near door 22, mounting nozzles on the side edges of floor 40 or mounting nozzles on the lower portions of the booth enclosing walls or door, mounting nozzles on floor 40 closer to the predetermined location or providing foot shields for a user to slide their feet under, with or without one or more foot rinse nozzles under the foot shields.

In yet another design, illustrated in FIG. 2, the foot rinser comprises a foot bath type reservoir 400 for holding foot rinser solution 404 sufficiently deep to cover the portions of a user's feet desired to be protected from staining or over staining by the artificial tanning composition. Though other designs are readily apparent, one suitable design includes at least one foot rinser solution inlet nozzle 402 and at least one drain 46. This design of foot rinser may also be equipped with agitation or sanitation mechanisms as desired and as are known in the art.

The foot rinser solution may be any biocompatible solution that will dilute the tanning composition below a concentration that would over-stain the user's feet. In a preferred embodiment, the foot rinser solution contains no artificial tanning active agents. Alternatively, the foot rinser solution may contain a more dilute concentration of the artificial tanning agent, or a different or different mixture of artificial tanning agent(s) than that applied to the rest of the body of a user. In another preferred embodiment, the foot rinse solution is water or a detergent solution. In one embodiment, the at least one rinse nozzle is coupled to a tap water source, optionally with a pressure regulator or compressor interposed to regulate the rinse solution pressure and/or rate of flow. In one preferred embodiment, the at least one rinse nozzle provides a fan shaped spray of rinser solution. In another embodiment, the at least one rinse nozzle provides a stream of rinser solution over the user's feet.

As with the feet as described above, it is known that different areas of the body can have different sensitivities to staining by artificial tanning agents. It is also often desirable to have a different darkness or hue of tan on different portions of the body. Examples of such differential coating needs or desires would include, but are not limited to less sensitivity of skin and/or a desire for darker tanning on the face, chest, back, and/or arms, and greater sensitivity of skin and/or a desire for lighter tanning of the knees, elbows, hands and/or feet. To accommodate these differential needs or desires, another aspect of the present invention provides for an apparatus for differentially applying a composition, as for example, but not limited to an artificial tanning composition, to a human body. The apparatus of this aspect of the present invention comprises an applicator for spray applying a first liquid containing a certain non-zero concentration of an active agent to one part of a body and for spray applying a second liquid having a different concentration of the active agent to a different part of the body. Though the active agent in one preferred embodiment is an artificial tanning agent, it should be appreciated that the apparatus can be used to differentially coat various other compositions on the body as desired. Such other compositions would include, but not be limited to sun tan lotions and therapeutic compositions for treatment of the skin or for adsorption through the skin.

In one preferred design for this aspect of the present invention, the first and second liquids are applied with the same nozzle or nozzles, and the apparatus varies the amount of each liquid being sprayed at a given time depending on the area of the body being sprayed. In this design, the first and second liquid may be sprayed individually or simultaneously as a mixture through the nozzles, as for example where the second liquid is a diluent and the concentration of active agent is varied by increasing or decreasing the ratio of the diluent to the active agent being sprayed at a given time, over a given area.

In another preferred design for this aspect of the present invention, the applicator uses different nozzles for the first and second liquids. In a preferred embodiment of this design, nozzles for the first liquid and nozzles for the second liquid may operate simultaneously. In another preferred embodiment, at least one nozzle for the second liquid operates substantially the entire time a nozzle for the first liquid is operating. In one specific embodiment, the second liquid has an active agent concentration of zero. In one preferred embodiment, at least one nozzle for the second liquid is directed on the feet of a user standing at the predetermined location in the booth.

In yet another embodiment of this aspect of the invention, at least one nozzle for the second liquid is directed at the feet of a user, while other nozzles may spray a mixture of the first liquid and second liquid to vary the concentration of active agent and/or the concentration and mixture of active agents in the spray directed to other areas of the body, as for example, but not limited to the back, chest, elbows, knees, hands, or face of a user.

In yet another embodiment of this aspect of the invention, the apparatus is equipped with a intelligent imagining scanner system, as for example, but not limited to a laser imaging scanner or an infrared scanner, and the apparatus senses the surface of the user's body to generate a computerized map of the user's body to identify specific body areas, and then controls the sprayer traversal rate and/or preferably the active agent concentration in the spray being applied through a specific nozzle or nozzles at a given time, to differentially apply composition to the body to achieve a differential coating of active agent or agents over different areas of the user's body.

In another aspect of the present invention, there is provided a sanitizing system comprising at least one wash-down nozzle mounted in the booth, operably coupled to a source of sanitizing solution to wash the booth. In a preferred embodiment, the at least one wash-down nozzle is a tank washing type nozzle, preferably a rotating 180 degree tank washing nozzle, though rotating tank washing nozzles up 360 degree may also be suitable. The sanitizing solution may be any cleaning and/or disinfecting solution including water, detergent solution, bactericidal solution, fungicidal solution, or any combination thereof.

FIG. 1 shows one embodiment of a wash-down system comprising a single washdown nozzle 32 mounted to the ceiling 30 of booth 10. Machine box 80, also shown in FIG. 11, houses a sanitizing solution reservoir 110, sanitizing solution pump 112, and sanitizing solution solenoid 114, to supply and control the flow of sanitizing solution through sanitizing solution supply line 116 to wash-down nozzle 32.

It is preferred that the wash-down system be configured to wash down the booth only when a user is not in the booth. In one embodiment, the system performs a wash-down operation upon activation by an operator, or automatically after a user exits the booth. In another embodiment, the wash-down system may be configured to wash-down the booth after a predetermined number of coating operations have been completed and a user is not in the booth.

In another aspect of the present invention, the spray booth is provided with a machine box housing the electrical and mechanical components of the apparatus. One skilled in the art will readily apprehend numerous suitable configurations for the necessary components to control the apparatus of the present invention. It is also to be understood that many of the components may be located at a distance from the booth and many may be configured to be shared by multiple spray booths.

Figure 11:
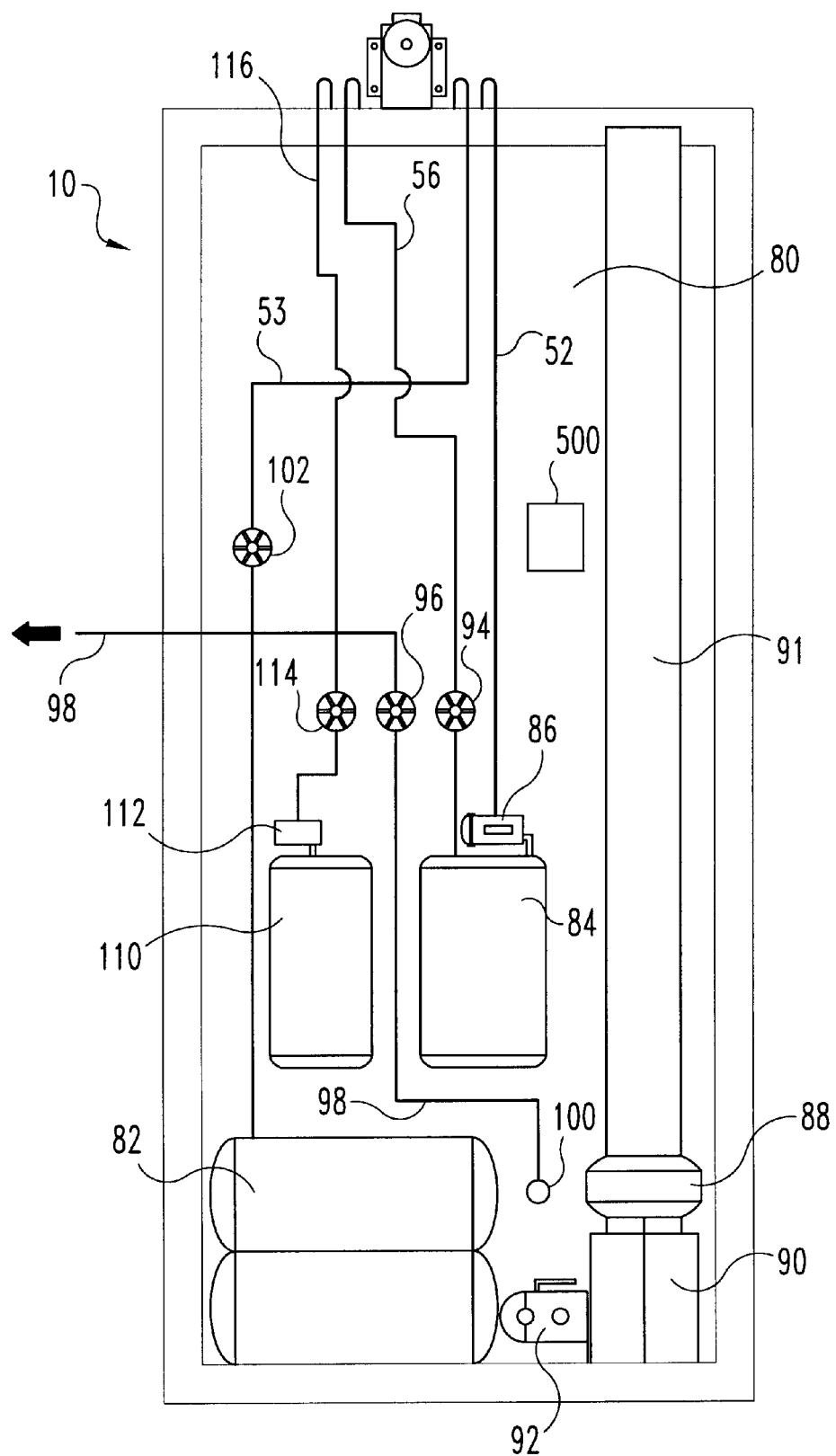
FIG. 11 is a schematic of one embodiment of a machine box for a spray booth according to the present invention.

FIG. 11 shows one suitable machine box 80 comprising tanning composition tank 84 coupled to tanning composition pump 86, which is in turn coupled to spray nozzles in the booth by supply line 52, and optionally through a mixing manifold, as for example, but without limitation, a mixing manifold 54 in FIGS. 1,3–5 and 9, or a mixing manifold in the machine box (not shown) with air/tanning composition supply line from the manifold to the nozzles in the box (not shown). Optionally, tanning composition return line 56 may provide return of composition to the tanning composition tank 84 as controlled by return solenoid 94. Air compressor 82 is coupled through appropriate pressure regulators (not shown) and air cut-off solenoid 102 and supply line 53 to the nozzles in the booth, optionally through a mixing manifold. Sanitizing solution tank 110 is coupled to sanitizing solution pump 112, which is in turn coupled to the wash-down nozzle in the booth through sanitizing solution solenoid 114 and supply line 116. Evacuation fan 88 draws excess over-spray from the booth through air filter 90 and vents the filtered air through vent tube 91. The evacuation fan 88 may draw over-spray laden air from booth 10 from any suitable port, as for example, but without limitation, exhaust port 48 shown in FIG. 1, and/or from an exhaust port over a collection reservoir under a grated floor, and/or from exhaust ports in the ceiling, or even the floor with appropriate liquid traps. Optional bilge pump 92 draws accumulated waste tanning composition, foot rinser solution and/or sanitizing solution from the one or more drains in the booth floor. Foot rinser solution feed line 98 couples a source of foot rinser solution to foot rinser in the booth through foot rinse solution solenoid 96. Controller unit 500 monitors and coordinates all components through electrical connections (not shown) along with appropriate feedback mechanisms using sensed pressures, temperatures, liquid levels, user heights, presence of a user, image of a user, drag on the traversal of the arm, arm location, feed rates, etc.

Figure 12:
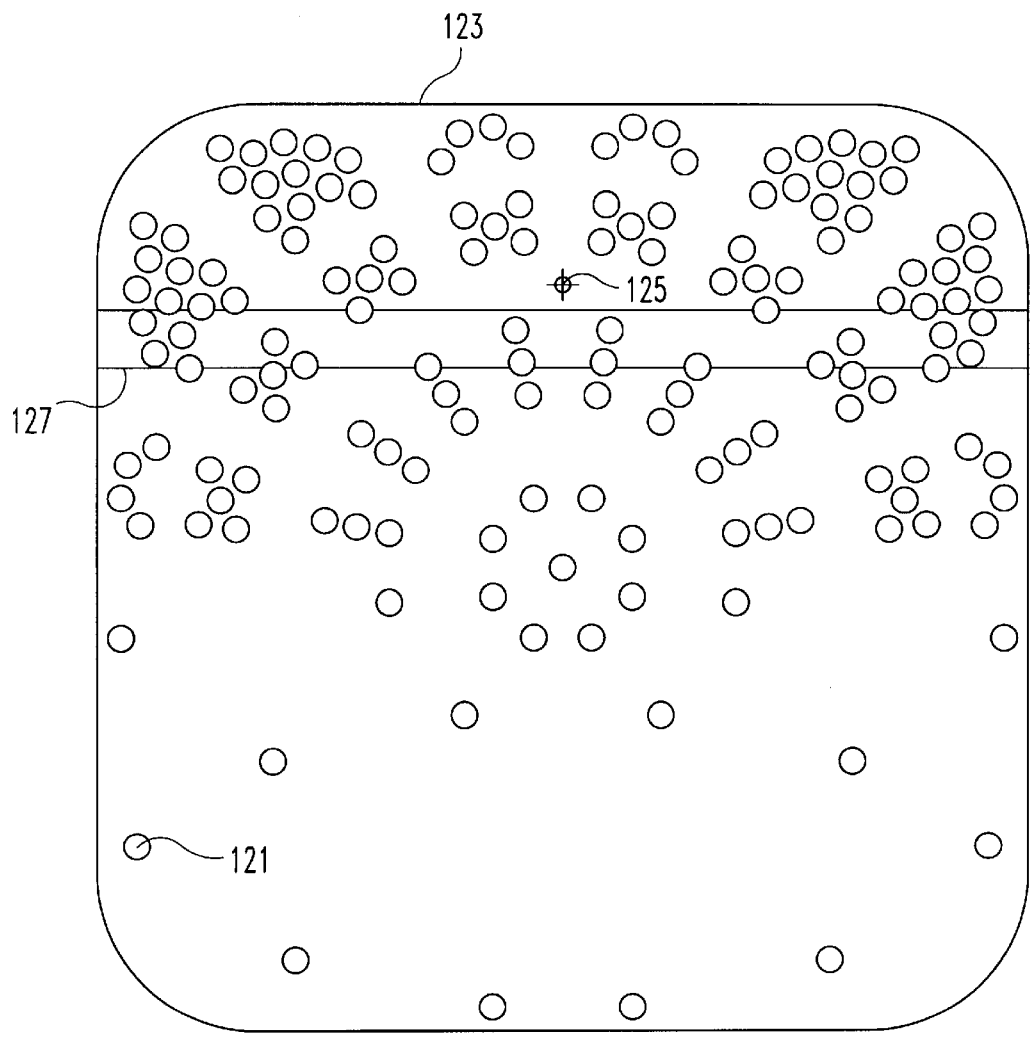
FIG. 12 is a plan view of a grate suitable for use in a spray booth according to the present invention.
Figure 13:
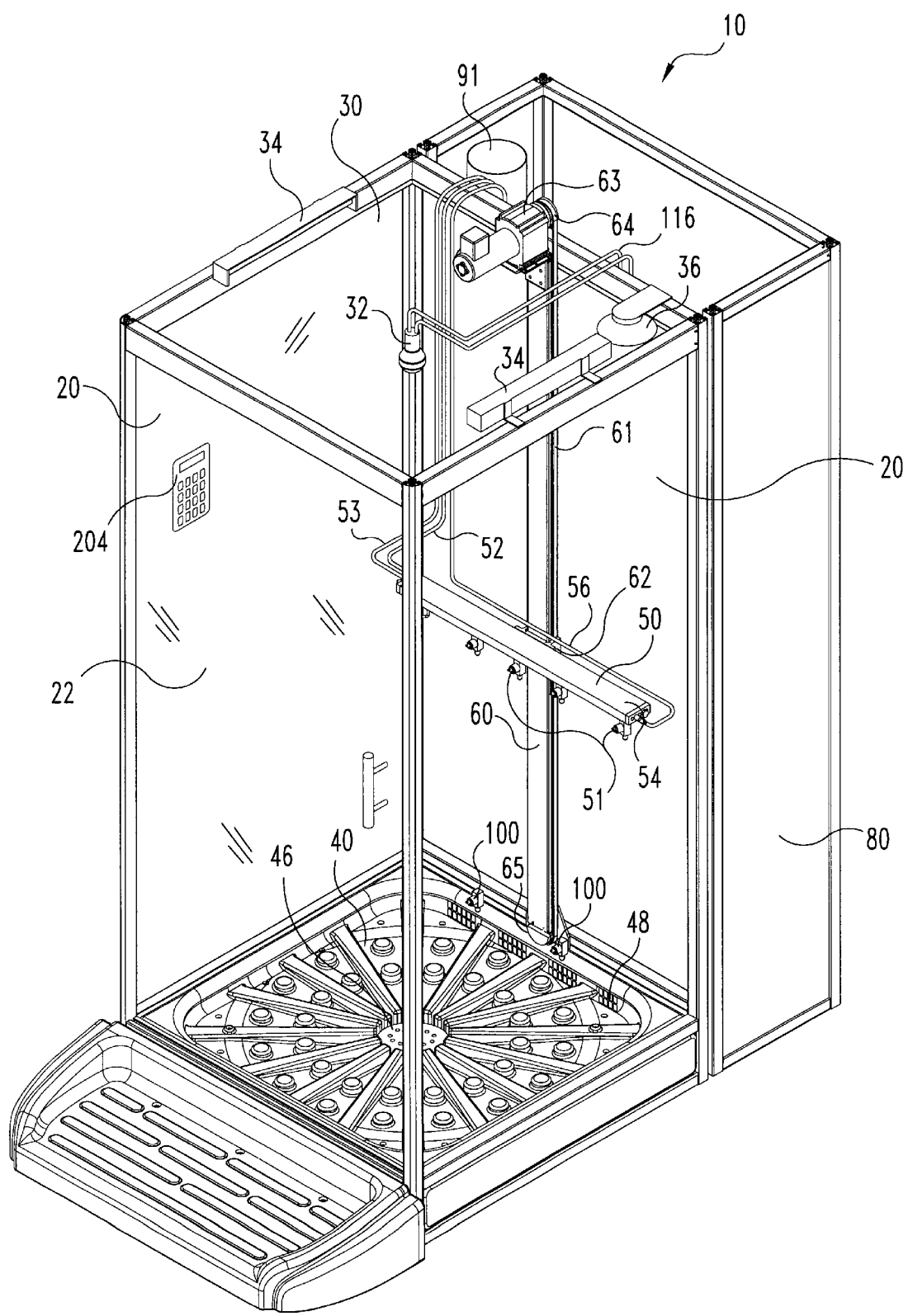
FIG. 13 is a perspective view of one embodiment of a spray booth adapted to use the grate of FIG. 12.
Figure 15:
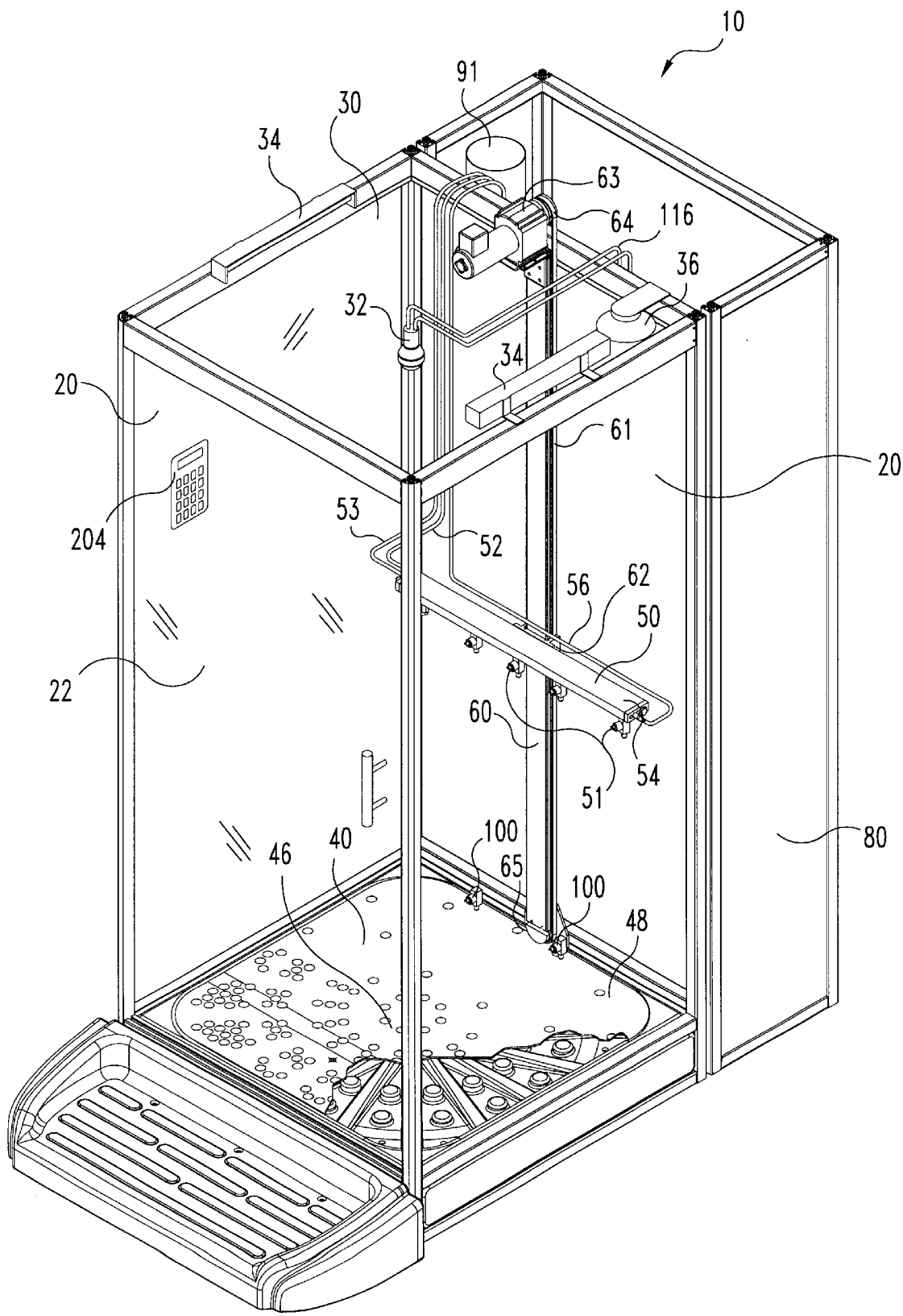
FIG. 15 is a perspective view of the spray booth of FIG. 13 with the grate of FIG. 12 in place and partially cut away to reveal the floor below the grate.
Figure 16:
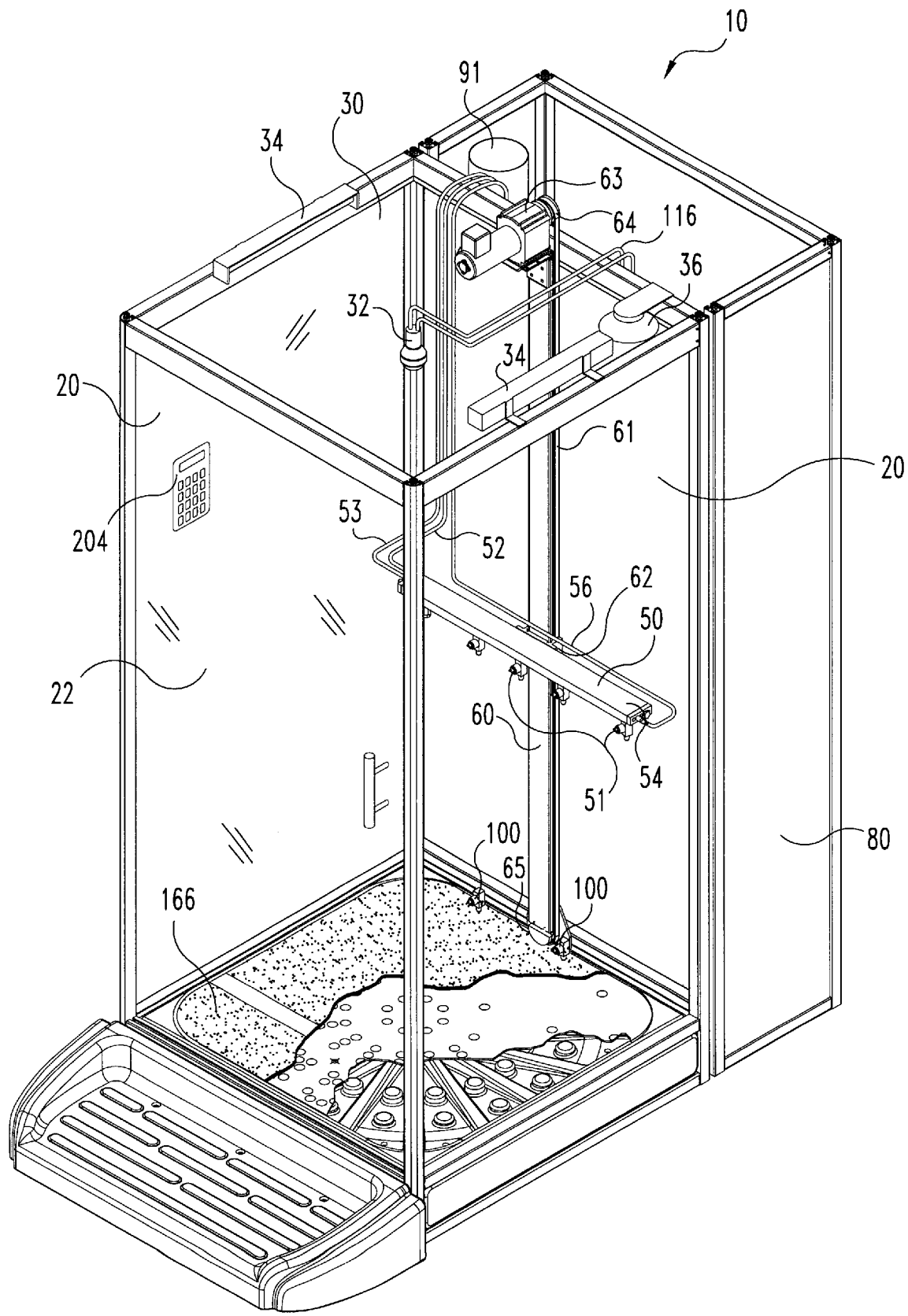
FIG. 16 is a perspective view of the spray booth of FIG. 13 with the grate of FIG. 12 in place and covered by a mat 166, shown partially cut away to show the grate and floor beneath.

FIG. 12 shows a grate, indicated generally at 123, suitable for use in a spray booth according to the present invention, similar to the one shown in FIG. 1. However, in a spray booth in which a grate 123 will be used, the exhaust port 48 is preferably located in the vertical edges of the floor 40, as shown in FIG. 13. The grate 123 is preferably rigid and has a pattern of holes 121 through it. The pattern of holes 121 preferably has a centroid 125 that is well away from the center of the grate 123, and on the side of the grate opposite to the spray nozzles 51. Thus, the cross section of passageways through the half of the grate 123 distal to the spray nozzles 51 is larger than through the half of the grate 123 proximal to the spray nozzles 51. As shown in FIG. 13, in certain preferred embodiments the floor 40 includes an approximately square well with rounded corners. The grate 123 preferably has dimensions sufficiently similar to those of the well in the floor 40 to permit it to easily be placed into the well, but, as shown in FIG. 15, without leaving a significant gap between the vertical edges of the well and the grate 123. The floor 40 is preferably adapted to support the edges and center of the grate 123 to create a plenum between the grate and floor into which air (including sunless tanning solution overspray) and foot rinsing solution can run from the section of the booth above the grate. The grate 123 is oriented within the well such that the centroid 125 of the pattern of holes 121 is furthest from the spray nozzles 51. In certain embodiments, the grate 123 is covered by a porous mat 166, as shown in FIG. 16. In certain embodiments, the porous mat 166 is made of rubber, or another substance such as a fabric containing elastomers. It can have the appearance of a woven component mat 166 with the spaces between the weaving providing porosity. The mat 166 provides a comfortable, non-slip surface for the user to stand on, but does not prevent the flow of air (or foot rinsing solution) through the grate into the space between the grate and the floor 40.

When the booth 10 is operated with the grate 123 in place, the evacuation fan 88 draws air from the booth 10, through the perforations in the rubber mat 166, through the pattern of holes 121 in the grate 123, into the plenum between the grate 123 and the floor 40, and out through the exhaust port 48, (where the sunless tanning agent over-spray is removed by filter 90, and the air may be then recirculated back into the booth near the top or exhausted). Because the flow of air is generally downward, excess tanning solution is pulled away from the user's hair and face. Also, it is pulled away from the ceiling 30, and any lights 34 or speaker 36 whose function might be impeded by the tanning solution. Because, in the preferred embodiments, the centroid 125 of the pattern of holes is on the opposite side of the certain location of the user from the spray nozzles 51, the vertical component of air flow on the distal side of the booth is higher than on the proximal side of the booth. The average flow of air in the booth above the plenum also has a horizontal component from the side of the booth 10 proximal to the spray nozzles 51 to the distal side. This helps to provide a more even and complete coating of the user's skin and further reduces turbulence and eddies.

In certain embodiments, the certain location at which the user is to be located is marked either on the grate 123 or on the mat 166 with some indicia visible to a user. In certain preferred embodiments, for example, the indicia is a stripe indicating where the user is to place the heels or balls of their feet. One example would be a white stripe on a black mat 166. FIG. 15 shows an embodiment in which the indicia is a stripe 127 on the grate 123. FIG. 16 shows a similar stripe on a porous mat 166 placed over the grate 123. In certain other embodiments (not shown), the indicia is an outline or other figure of feet on which a user may stand. In certain preferred embodiments, the indicia is a shape or region that is a substantially different color from the rest of the mat 166 or grate 123. In others, the indicia is a pattern substantially different from the rest of the lower surface of the booth. Regardless of the specific indicia used, the indicia indicates, without ambiguity from other nearby colors or patterns, where a user should stand in order to place their body in the certain location, at which the spray nozzles produce approximately the most even deposition of sunless tanning solution.

Figure 14:
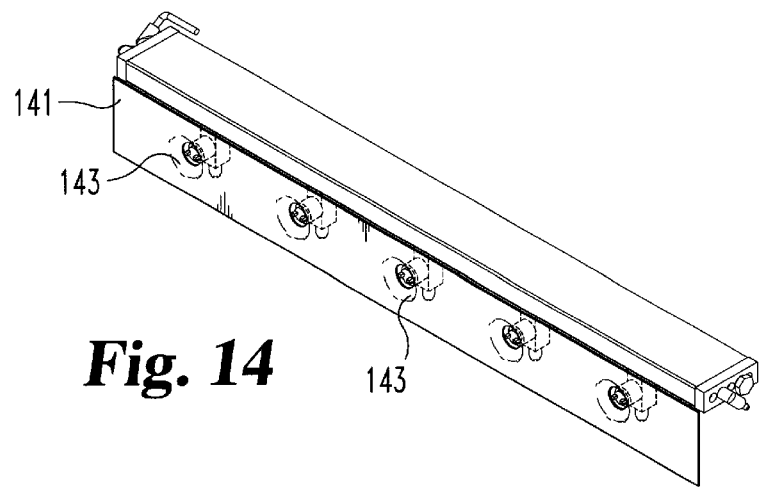
FIG. 14 is a perspective view of a protective plate suitable to be affixed to the movable arm of FIG. 3.

In certain embodiments, as shown in FIG. 14, a protective plate 141 having a set of apertures 142 corresponding to the spray nozzles 51 is positioned with the spray nozzles 51 protruding through the apertures. Preferably the apertures of the nozzles 51 are spaced far enough from the face of the protective plate 141 to avoid creating turbulence in the spray patterns. In certain preferred embodiments, for example, the apertures are positioned in hemispherical dimples 143, as shown in FIG. 14. The dimples permit the apertures of the nozzles to be flush with the face of the protective plate 141, yet have sufficient open space behind the aperture of each of the nozzles 51 to substantially prevent turbulence in the spray pattern that would otherwise be created by proximity to the protective plate 141. In certain other embodiments, the nozzles 51 simply protrude through the apertures 142 far enough to create the necessary separation between the nozzles' 51 apertures and the face of the protective plate 141.

In certain preferred embodiments a water heater is included in the foot rinser solution feed line 98, for example between the foot rinse solution solenoid and the foot rinse nozzles 100. In such embodiments the water heater is preferably made a part of the tanning booth assembly, very close to the foot rinse nozzles 100, rather than being a separate device more remotely located. This provides an advantage in control of the temperature of the foot wash. In this way the foot rinse solution can be heated to a comfortable temperature before being sprayed on the user's feet.

In certain preferred embodiments, the tanning composition pump 86 is a peristaltic pump.

In certain preferred embodiments the booth 10 is further equipped with electronic communications equipment, such as a modem or a network communications card (either to permit communications with a local area network or another network, such as the Internet), to permit remote programming or control of one or more operations parameters, such as pump pressure or the tanning solution-to-air mixture ratio. The communications equipment may also be used for other remote controls, such as monitoring activation of the booth in order to schedule periodic maintenance, such as refilling with sunless tanning solution, or to monitor usage to determine appropriate fees for use of the booth.

While the invention and its preferred embodiments have been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected as set forth in the following claims.

What is claimed is:

1. An apparatus for applying a composition to a human body, comprising:
   a substantially enclosed volume large enough to encompass a human body,
   an applicator substantially on one side of the apparatus for spray applying the composition;
   a fan positioned to cause air to pass through the substantially enclosed volume;
   flow control pathways to provide a net horizontal component of flow of air away from said applicator; and
   a foot rinser positioned to rinse the feet of a human body standing within the substantially enclosed volume.

2. The apparatus of claim 1 in which there additionally is a vertical component of air flow.

3. The apparatus of claim 2 in which there is a grate at the lower portion of the apparatus that has a larger cross section of passageways distal to the spray applicator than proximal to the spray applicator.

4. The apparatus of claim 2 in which the vertical component flows downwardly.

5. The apparatus of claim 4 in which a lower part of a side of the apparatus distal to the spray applicator has a higher rate of vertical flow than a lower part of a side proximal to the spray applicator.

6. An apparatus for applying a composition to a human body comprising:
   a substantially enclosed volume large enough to encompass a human body and having a proximal and a distal side,
   an applicator substantially on the proximal side of the apparatus for spray applying the composition;
   a fan positioned to cause air to pass through the substantially enclosed volume;
   flow control pathways to provide a more rapid net vertical flow of air near the lower portion of the distal side of said volume than near the lower portion of the proximal side; and
   a foot rinser positioned to rinse a user's feet when the user stands at a certain position.

7. An apparatus for applying a composition to a human body, comprising:
   a substantially enclosed volume large enough to encompass a human body,
   an applicator substantially on one side of the apparatus for spray applying the composition;
   a foot rinser positioned to spray a user's feet with a foot rinsing solution when the user stands at the certain position;
   a heater for the foot rinsing solution.

8. The apparatus of claim 7, wherein the composition comprises a non-zero concentration of a tanning solution.

9. The apparatus of claim 8, wherein the heater does not heat the sunless tanning composition before the spray nozzle sprays it onto the human body.

10. An apparatus for applying a sunless tanning composition to a human body, the apparatus comprising a peristaltic pump.

11. The apparatus of claim 10, wherein the peristaltic pump is used to mix air and the sunless tanning composition before it is applied to the human body.

* * * * *